(12) United States Patent
Sirtori et al.

(10) Patent No.: US 6,617,134 B1
(45) Date of Patent: Sep. 9, 2003

(54) DIMER OF MOLECULAR VARIANT OF APOLIPOPROTEIN AND PROCESSES FOR THE PRODUCTION THEREOF

(75) Inventors: Cesare Sirtori, Milan (IT); Guido Franceschini, Milan (IT); Lars Abrahmsén, Stockholm (SE); Erik Holmgren, Lidingö (SE); Mats Lake, Lidingö (SE); Björn Nilsson, Sollentuna (SE); Joanna Chmielewska, Stockholm (SE); Peter Lind, Uppsala (SE)

(73) Assignee: Esperion Therapeutics, Inc., Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/259,434

(22) Filed: Mar. 1, 1999

Related U.S. Application Data

(63) Continuation of application No. 08/104,063, filed on Nov. 4, 1993, now Pat. No. 5,876,968.

(30) Foreign Application Priority Data

Dec. 13, 1991 (SE) ................................................ 9103701
Dec. 11, 1992 (WO) ............................... PCT/SE92/00858

(51) Int. Cl.[7] ................................................ C12P 21/04
(52) U.S. Cl. ........................... 435/69.7; 514/2; 530/350
(58) Field of Search ................................. 435/69.7, 217, 435/252.3, 252.33, 320.1; 514/2; 530/350; 536/22.1, 23.1, 22.2, 23.5

(56) References Cited

U.S. PATENT DOCUMENTS 5,876,968 A * 3/1999 Sirtori et al. ............... 435/69.7

FOREIGN PATENT DOCUMENTS

EP 267 703 A1 5/1998
WO 90/12879 * 11/1990

OTHER PUBLICATIONS

Franceschini et al. J. Biol. Chem. 265(21):12224–12231, Jul. 25, 1990.*
Franceschini et al. J. Biol. Chem. 257(17):9926–9930, 1982.*
Amann, et al., "Tightly regulated tac promoter vectors useful for the expression of unfused and fused proteins in *Escherichia coli*," *Gene* 69(2):301–15 (1988).
Badimon, et al., "High density lipoprotein plasma fractions inhibit aortic fatty streaks in cholesterol–fed rabbits," *Lab Invest* 60(3):455–61 (1989).
Badimon, et al., "Regression of atherosclerotic lesions by high density lipoprotein plasma fraction in the cholesterol–fed rabbit," *J Clin Invest* 85(4):1234–41 (1990).
Boyer, et al., "A complementation analysis of the restriction and modification of DNA in *Escherichia coli*," *J Mol Biol* 41(3):459–72 (1969).
Bressan, et al., "pUEX, a bacterial expression vector related to pEX with universal host specificity," *Nucleic Acids Res* 15(23):10056 (1987).
Brewer, et al., "The amino acid sequence of human APOA–I, an apolipoprotein isolated from high density lipoproteins," *Biochem Biophys Res Commun* 80(3):623–30 (1978).
Chueng, et al., "Characterization of A–I–containing lipoproteins in subjects with A–I Milano variant," *Biochim Biophys Acta* 960(1):73–82 (1988).
Esper, et al., "Effect of One Month Infusion of HDL on Plasma Lipids and Lipoproteins of WHHL Rabbits," *Arteriosclerosis* 7:523a (1987).
Franceschini, et al., "Relation between the HDL apoproteins ans AI isoproteins in subjects with the AI–M abnormality," *Metabolism* 30:502–509 (1981).
Gergen, et al., Filter replicas and permanent collections of recombinant DNA plasmids, *Nucleic Acids Res* 7(8):2115–36 (1979).
Greenfield, et al., "Computed Circular Dichroism Spectra for the Evaluation of Protein Conformation," *Biochemistry* 8:4108–4116 (1969).
Gualandri, et al., $AI_{Milano}$ apoprotein identification of the complete kindred and evidence of a dominant genetic transmission, *Am J Hum Genet* 37(6):1083–97 (1985).
Havel, et al., "The distribution and chemical composition of ultracentrifugally separated lipoproteins in human serum," *J. Clin. Invest.* 24: 1345–1355 (1955).
Lowry, et al., "Protein measurement with the Folin phenol reagent," *J. Biol. Chem.* 193:265–275 (1951).
Maciejko, et al., "Apolipoprotein A–I as a marker of angiographically assessed coronary–artery disease," *N Eng J Med.* 309(7):385–9 (1983).
Maciejko, et al., "Intravenous Administration of Apoprotein A–I Protects the Aorta from Dietary Cholesterol–Induced Atherosclerosis," *Arteriosclerosis* 2:407a (1982).

(List continued on next page.)

Primary Examiner—Karen Cochrane Carlson
(74) Attorney, Agent, or Firm—Holland & Knight LLP

(57) ABSTRACT

Substantially pure dimers of Apolipoprotein AI-Milano (APO-AI-M/APO AI-M) were isolated from plasma and characterized. Apolipoprotein AI-M dimer can also be produced in a recombinant *Escherichia coli* system. Pharmaceutical compositions comprising the ApoAI-AI-M/ApoAI-M are described. Patients with atherosclerosis or cardiovascular diseases can be treated with the dimer. Medicaments containing the dimer can also be used to prevent thrombosis in different clinical circumstances, both at the arterial and at the venous level. The dimer can also act as a prodrug for the monomer.

18 Claims, 13 Drawing Sheets

OTHER PUBLICATIONS

Figure 1:
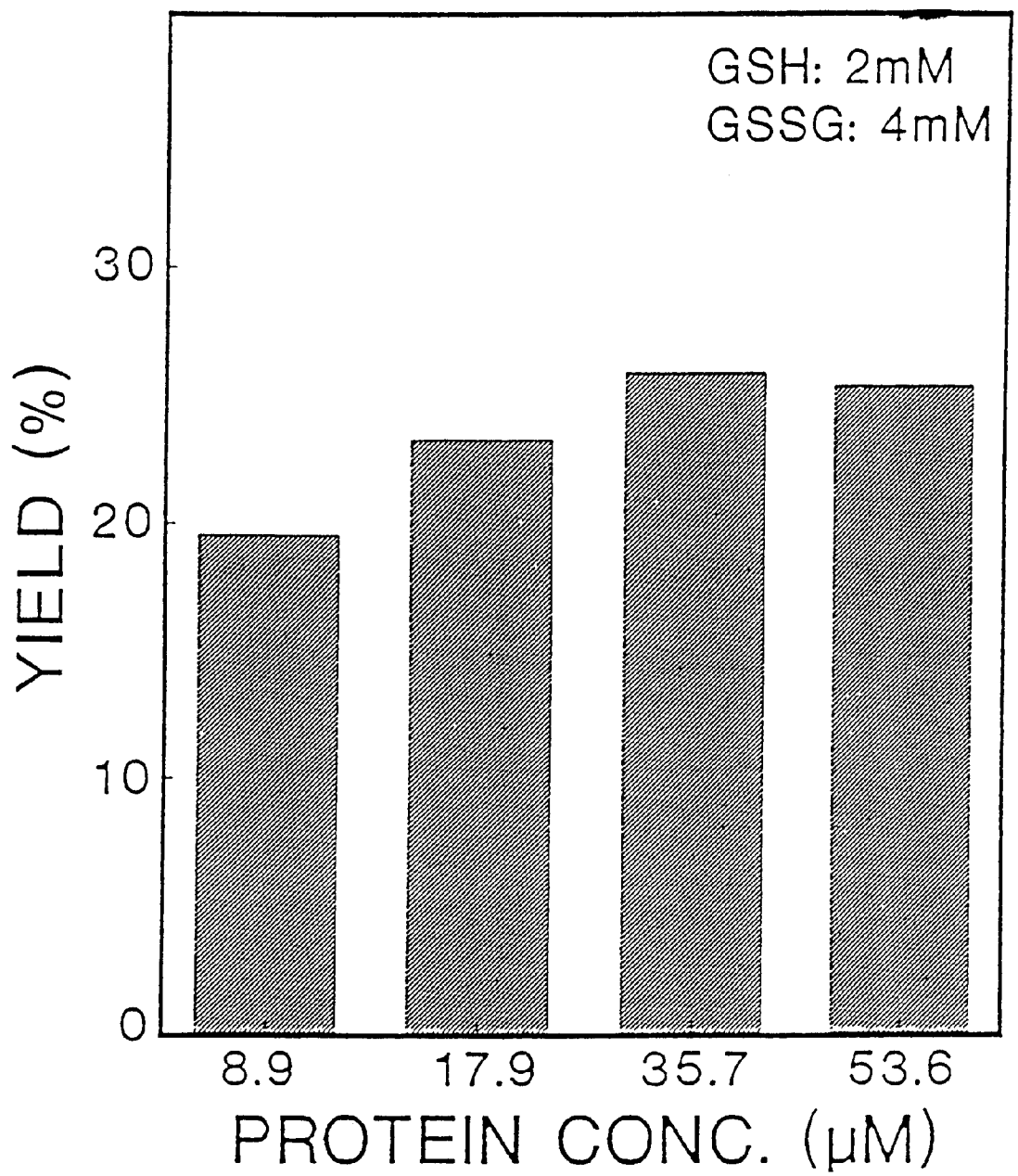

Matz, et al., "Micellar complexes of human apolipoprotein A–I with phosphatidylcholines and cholesterol prepared from cholate–lipid dispersions," *J Biol Chem.* 257(8):4535–40 (1982).

Maurer, et al., "Gene regulation at the right operator (OR) bacteriophage lambda. I. OR3 and autogenous negative control by repressor," *J Mol Biol.* 139(2):147–61 (1980).

Miller, et al., "The Tromso heart–study. High–density lipoprtein and coronary heart–disease: a prospective case–control study," *Lancet* 1(8019):965–8 (1977).

Nichols, et al., "Characterization of discoidal complexes of phosphatidylcholine, apolipoprotein A–I and cholesterol by gradient gel electrophoresis," *Biochim Biophys Acta.* 750(2):353–64 (1983).

Nichols, et al., "Nondenaturing polyacrylamide gradient gel electrophoresis," *Methods Enzymol.* 128:417–31 (1986).

Nilsson, et al., "Immobilization and purification of enzymes with staphylococcal protein A gene fusion vectors," *EMBO J.* 4(4):1075–80 (1985).

Oka, et al., "Nucleotide sequence of the kanamycin resistance transposon Tn903," *J Mol Biol* 147(2):217–26 (1981).

Owens, et al., "Apolipoprotein A–I and its amphipathic helix peptide analogues inhibit human immunodeficiency virus–induced syncytium formation," *J Clin Invest* 86(4):1142–50 (1990).

Pigiet, et al., "Thioredoxin–catalyzed refolding of disulfide–containing proteins," *Proc Natl Acad Sci USA.* 83(20):7643–7 (1986).

Ragone, et al., "Determination of tyrosine exposure in proteins by second–derivative spectroscopy," *Biochemistry* 23(8):1871–5 (1984).

Saku, et al., "Activation of fibrinolysis by apolipoproteins of high density lipoproteins in man," *Thromb Res.* 39(1):1–8 (1985).

Sedlis, et al., "Plasma apoproteins and the severity of coronary artery disease," *Circulation* 73(5):978–86 (1986).

Segrest, et al., "A molecular theory of lipid–protein interactions in the plasma lipoproteins," *FEBS Lett* 38(3):247–58 (1974).

Seilhammer, et al., "Isolation and DNA sequence of full–length cDNA and of the entire gene for human apolipoprotein AI—discovery of a new genetic polymorphism in the apo AI gene," *DNA* 3(4):309–17 (1984).

Sharpe, et al., "Human apolipoproteins AI, AII, CII and CIII. cDNA sequences and mRNA abundance," *Nucleic Acids Res* 12(9):3917–32 (1984).

Srinivas, et al., "Antiviral effects of apolipoprotein A–I and its synthetic amphipathic peptide analogs," *Virology* 176(1):48–57 (1990).

Stein, et al., "The removal of cholesterol from aortic smooth muscle cells in culture and Landschutz ascites cells by fractions of human high–density apolipoprotein," *Biochim Biophys Acta.* 380(1):106–18 (1975).

Viera, et al., "The pUC plasmids, an M13mp7–derived system for insertion mutagenesis and sequencing with synthetic universal primers," *Gene* 19(3):259–68 (1982).

Weisgraber, et al. "Identification of the disulfide–linked homodimer of opolipoptein E3 in plasma. impact on receptor binding activity," *J Biol Chem* 266(18):12029–34 (1991).

Weisgraber, et al., "Apolipoprotein A–IMilano. Detection of normal A–I in affected subjects and evidence for a cysteine for arginine substitution in the variant A–I," *J Biol Chem.* 258(4):2508–13 (1983).

Whayne, et al., "Plasma apolipoprotein B and VLDL–, LDL–, and HDL–cholesterol as risk factors in the development of coronary artery disease in male patients examined by angiography," *Atherosclerosis* 39(3):411–24 (1981).

* cited by examiner

Linker-ΔApoAI-Eco

Length of linker-DApoAI-Eco(circular): 28 bp;
    Simple Restriction from: 1 to: 28;

✕ AvaII            ✕ BanII
                       ✕ Bsp1286
    ✕ EcoRI            ✕ DsaI
                       ✕ EcoT14I
                       ✕ NcoI
                       ✕ NspII
                       ✕ StyI
    GAATTCGGAC CCACCGCAGA GCCCATGG
     AsnSerAsp ProProGlnSerProTrp
            10         20      28

DApoAI-Eco-5 : 22 bp; +1 at: 1;

5'-AATTCGGACC CACCGCAGAG CC
            10         20 22

DApoAI-Eco-3 : 22 bp; +1 at: 1;

5'-CATGGGCTCT GCGGTGGGTC CG
            10         20 22

Figure 4

DIMER OF MOLECULAR VARIANT OF APOLIPOPROTEIN AND PROCESSES FOR THE PRODUCTION THEREOF

This application is a continuation of application Ser. No. 08/104,063, filed Nov. 4, 1993 under 35 U.S.C. §371, entitled "DIMER OF MOLECULAR VARIANT OF APOLIPOPROTEIN AND PROCESS FOR THE PRODUCTION THEREOF," by Cesare Sirtori, Guido Franceschini, Lars Abrahmsén, Erik Holmgren, Mats Lake, Björm Nilsson, Joanna Chmielewska, and Peter Lind, which issued on Mar. 2, 1999, as U.S. Pat. No. 5,876,968. U.S. Pat. No. 5,876,968, issued Mar. 2, 1999, is hereby incorporated herein by reference.

The present invention refers to the substantially pure dimer of apolipoprotein AI-Milano (ApoAI-M/ApoAI-M) and pharmaceutical compositions containing this dimer. It also relates to the process for the preparation by recombinant technique as well as by isolation from plasma. The product may be used for the treatment of atherosclerosis and cardiovascular diseases and as a retard formulation of the ApoAI-M

BACKGROUND

The clear correlation between elevated levels of serum cholesterol and the development of coronary heart disease (CHD) has been repeatedly confirmed, based on epidemiological and longitudinal studies. The definition, however, of complex mechanisms of cholesterol transport in plasma, has allowed the recognition of a selective function of circulating lipoproteins in determining the risk for CHD.

There are, in fact, four major circulating lipoproteins: chylomicrons (CM), very low density (VLDL), low density (LDL) and high density (HDL) lipoproteins. While CM constitute a short-lived product of intestinal fat absorption, VLDL and, particularly, LDL are responsible for cholesterol transport into tissues, including for example the arterial walls. In contrast, HDL are directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies (e.g. Miller et al. Lancet, 1977:965–968 and Whayne et al. Atherosclerosis 1981;39:411–419). In these, the elevated levels of LDL, less so of VLDL, seem to be clearly associated with an increased cardiovascular risk, whereas high HDL levels seem to confer cardiovascular protection. The protective role of HDL has been further strongly supported by the in vivo studies, showing that HDL infusions into rabbits may hinder the development of cholesterol induced arterial lesions (Badimon et al, Lab. Invest. 60, 455–61, 1989)) and/or induce regression of same (Badimon et al, J Clin Invest. 85, 1234–41, 1990).

Recent interest in the study of the protective mechanism/s of HDL has been focussed on apolipoprotein AI (ApoAI), the major component of HDL. High plasma levels of ApoAI are associated with reduced risk of CHD and presence of coronary lesions (Maciejko et al,. N Engl J Med 1983;309:385–389, Sedlis et al,. Circulation 1986;73:978–984).

Plasma ApoAI is a single polypeptide chain of 243 amino acids, whose primary sequence is known (Brewer et al, Biochem Biophys Res Commun 1978;80:623–630). ApoAI is synthesized as a 267 amino acid precursor in the cell. This pre-pro-apoliprotein is processed by N-terminal cleavage first intracellularly where 18 amino acids are lost and then with a further cleavage of 6 amino acids in the plasma or the lymph by the activity of specific proteases.

The major structural requirement of the ApoAI molecule is believed to be the presence of repeat units of 11 or 22 amino acids, presumed to exist in amphipathic helical conformation (Segrest et al, FEBS Lett 1974;38:247–253). This structure allows for the main biological activities of ApoAI, i.e. lipid binding and lecithin cholesterol acyl transferase (LCAT) activation. Another recently described property of ApoAI is its antiviral activity. This has been reported from in vitro studies and is exerted both against Herpes virus strains (Srinivas R V et al, Virology, 1756, 48–57, 1990) and also against the Human Immunodeficiency virus, HIV, (Owe et al,., J Clin Invest, 86, 1142–50, 1990). This activity seems to be exerted by way of an interaction between amphipatic helical portions of ApoAI and envelope glycoproteins of the viruses.

In vitro studies indicate that complexes of ApoAI and lecithin can promote the efflux of free cholesterol from cultured arterial smooth muscle cells (Stein et al,. Ciochem Biophys Acta 1975;380:106–118). By this mechanism HDL can also reduce the proliferation of these cells (Yoshida et al, Exp Mol Pathol 1984;41 :258–266).

More recently, the infusion of ApoAI or of HDL in experimental animals has been shown to exert significant biochemical changes, as well as to reduce the extent and severity of atherosclerotic lesions. After an initial report by Maciejko and Mao (Arteriosclerosis 1982;2:407a), Badimon et al, (see the two quoted studies above) found that they could significantly reduce the extent of atherosclerotic lesions (−45%) and their cholesterol ester content (−58.5%) in cholesterol-fed rabbits, by infusing HDL (d=1.063–1.325 g/ml). They also found that the infusions of HDL led to a close to a 50% regression of established lesions.

It was able to be shown also (Esper et al. Arteriosclerosis 1987;7:523a) that infusions of HDL can markedly change the plasma lipoprotein composition of Watanabe rabbits with inherited hypercholesterolemia, which develop early arterial lesions. In these, HDL infusions can more than double the ratio between the protective HDL and the atherogenic LDL.

The potential of HDL to prevent arterial disease in animal models has been further stimulated by the observation that ApoAI can exert a fibrinolytic activity in vitro (Saku et al, Thromb Res 1985;39:1–8). Ronneberger (Xth Int Congr Pharmacol, Sidney 1987, p 990) demonstrated that extractive ApoAI can increase fibrinolysis in beagle dogs and in Cynomologous monkeys. A similar activity can be noted in vitro on human plasma. This author was able to confirm a reduction of lipid deposition and arterial plaque formation in ApoAI treated animals.

The apolipoprotein AI-Milano (ApoAI-M) is the first described molecular variant of human ApoAI (Franceschini et al, J Clin Invest 1980;66:892–900). It is characterized by the substitution of Arg 173 with Cys (Weisgraber et al, J Biol Chem 1983;258:2508–2513). The mutant apoprotein is transmitted as an autosomal dominant trait and 8 generations of carriers have been identified (Gualandri et al, Am J Hum Genet 1984;37:1083–1097).

The status of the ApoAI-M carrier individual is characterized by a remarkable reduction in HDL-cholesterol level. In spite of this, the affected subjects do not apparently show any increased risk of arterial disease; indeed, by examination of the genealogic tree it appears that these subjects may be "protected" from atherosclerosis.

The mechanism of the possible protective effect of ApoAI-M in the carriers seems to be linked to a modification in the structure of the mutant apolipoprotein, with the loss of one alpha-helix and an increased exposure of hydrophobic residues (Francheschini et al,. J Biol Chem 1985;260:1632–1635). The loss of the tight structure of the multiple alpha-helices leads to an increased flexibility of the molecule, which associates more readily with lipids, compared to normal AI. Moreover, apolipoprotein/lipid complexes are more susceptible to denaturation, thus suggesting that lipid delivery is also improved in the case of the mutant.

The therapeutic use of the apolipoprotein ApoAI-M mutant is presently limited by the lack of a method allowing the preparation of said apolipoproteins in sufficient amount and in a suitable form.

Another very specific feature of the ApoAI-M, is its capacity to form dimers with itself and complexes with ApoAII, in both cases because of the presence of the Cys residue. From studies of blood fractions containing a mixture of Apolipoproteins, there were indications, showing that the presence of dimers and complexes in the circulation may be responsible for the increased elimination half-life of these in the carriers, recently described in clinical studies (Gregg et al,. NATO ARW on Human Apolipoprotein Mutants: From Gene Structure to Phenotypic Expression, Limone SG, 1988).

ApoAI-M dimers (ApoAI-M/ApoAI-M) act as an inhibiting factor in the interconversion of HDL particles in vitro (Franceschini et al, J Biol Chem 1990;265:12224–12231).

Earlier studies of mixtures containing the dimer have been based on ApoAI-M separated from natural blood from persons with Apo AI-M, which has thus only been obtainable in small quantities.

The difficulty of producing ApoAI and particularly ApoAI-M from plasma fractionation is quite considerable (Franceschini et al, J Biol Chem 1985;260:16321–16325). The isolation and production cannot be done on a big scale, as only a small amount of the raw material is available. Furthermore, there are several risks associated with plasma fractionation products, such as contamination with infectious agents. It is essential that this is avoided.

Attempts have been made to produce human ApoAI, by way of the recombinant DNA technology. In the European patent publication No. 0267703 the preparation of ApoAI from *E.coli* is described. The process describes a chimeric polypeptide where the ApoAI moiety is fused to the N-terminal amino acid residues of beta-galactosidase or to one or more IgG-binding domains of Protein A, or to the pro sequence of human ApoAI.

The expression of ApoAI and ApoAI-M in yeast strains and the use of the produced components in the treatment of atherosclerosis and cardiovascular diseases is disclosed in WO90/12879. The genes encoding the ApoAI and ApoAI-M were provided with DNA-sequences encoding a yeast-recognizable secretion and processing signals fused upstream to the gene for the mature proteins. A modified MF-alpha-1-leader sequence was used in which the last residues were: HisGlySerLeuAspLysArg.

PRESENT INVENTION

We have now surprisingly found that the purified dimer Apo AI-M/ApoAI-M has a prolonged plasma half-life compared to the monomer ApoAI-M, further that it has a markedly improved fibrinolysis stimulating property compared to normal ApoAI e.g. its ability to directly activate plasminogen (which normal ApoAI does not), an observation that can be of biological importance, and also the possibility to act as a prodrug for ApoAI-M. It also forms reconstituted HDL (high density lipoprotein) particles of unique size which is not found in recombinant HDL particles containing ApoAI-M or ApoAI.

The present invention relates to substantially pure dimers of apolipoprotein AI-Milano, hereafter called ApoAI-M/ApoAI-M, with a purity of at least 90%, preferably at least 98%, which for the first time has been isolated and characterized from plasma and which also has been produced by recombinant methods. It also relates to pharmaceutical compositions comprising the Apo AI-M/ApoAI-M, optionally together with a stabilizing agent e.g. stabilizing lipid compound such as a phospholipid and/or a carrier.

The pharmaceutical compositions can also contain a lipid lowering agent and/or other medicament already known in the treatment of atherosclerosis and cardiovascular diseases, such as heparin, heparin fractions, and heparin fragments or lipid lowering agents.

Apolipoprotein ApoAI-M can be produced by a) producing Apolipoprotein AI-Milano by recombinant technology as intracellular fusion protein in *E coli*, cleaving off Apolipoprotein AI-Milano with formic acid and therefter converting any monomer present to the dimer or b) producing Apolipoprotein AI-Milano by recombinant technology in which the Apolipoprotein AI-Milano, monomer and dimer, is secreted into the bacterial culture medium in an expression system in *E coli* and any monomer present thereafter converted to the dimer and purifying the dimer to a substantially pure form.

According to a) ApoAI-M is produced as a fusion protein intracellularly in the bacteria. The fusion partner is a modified IgG binding domain from protein A, and a cleavage site for formic acid is designed between the fusion partner and ApoAI-M. After lysis of the bacteria, fusion protein was purified on immobilized IgG and cleaved with formic acid. The presence of ApoAI-M and the dimer was showed by Western blotting techniques on a SDS gel electrophoresis.

In example 3 is shown that processed ApoAI-M could be produced in recombinant *E. coli* and that dimers are formed. However the use of formic acid gives a product truncated with two amino acids in its N-terminal. This truncation is not supposed to alter the activity of the ApoAI-M molecule.

The system according to b) is shown in example 4, in which the completely correct molecule is formed.

The claimed dimer of ApoAI-M can also be obtained c) by collecting plasma from Apolipoprotein AI-Milano carriers, isolating the HDL apolipoproteins, separating the dimer by use of chromatography, e.g. by Sephacryl chromatography, in several steps or d) by collecting plasma from Apolipoprotein AI-Milano carriers, purificating the monomer and thereafter converting to the dimer and purifying the dimer to a substantially pure form.

It is important that the separation under c) is effected in several steps and preferably on a long column, such as 300 cm.

If monomer is present, it should always be converted to the dimer form, as shown in the examples below.

The invention includes the method for the treatment of atherosclerosis and cardiovascular diseases and use of the dimer for the preparation of a medicament. The dimer can also be acting as a prodrug for the monomer for the treatment of atherosclerosis and cardiovascular diseases.

This medicament can be used for the treatment of atherosclerosis and cardiovascular diseases and for the prevention and treatment of major cardiocirculatory ailments such as myocardial infarction, unstable angina, acute peripheral vascular occlusions and restenosis after coronary angioplasty.

When chronic arterial conditions are treated, both the coronaries and also peripheral arteries, which are characterized by occlusive plaque, are treated. The dimers will be used for infusion per se with the objective of inducing removal of fat from the plaques or optionally in association with established treatments of atherosclerosis and cardiovascular diseases, such as the use of heparin, heparin fractions and heparin fragments and/or drugs reducing the circulation levels of atherogenic lipoproteins.

The medicament containing the dimer can be used for the prevention and treatment of thrombosis in different clinical circumstances and be used in the stimulation of fibrinolysis.

Amphipathic structures are present to a high extent in the Apo AI-M dimer and the dimer is supposed to have an antiviral effect.

Now for the first time, by the use of the present invention, it has been possible to produce the dimer in an essentially pure form, more than 90% and as much as more than 98% and also to show that this product has a surprisingly better effect on biological systems as compared to ApoAI, which has been shown in our exemples 7–10 below.

Figure 2:
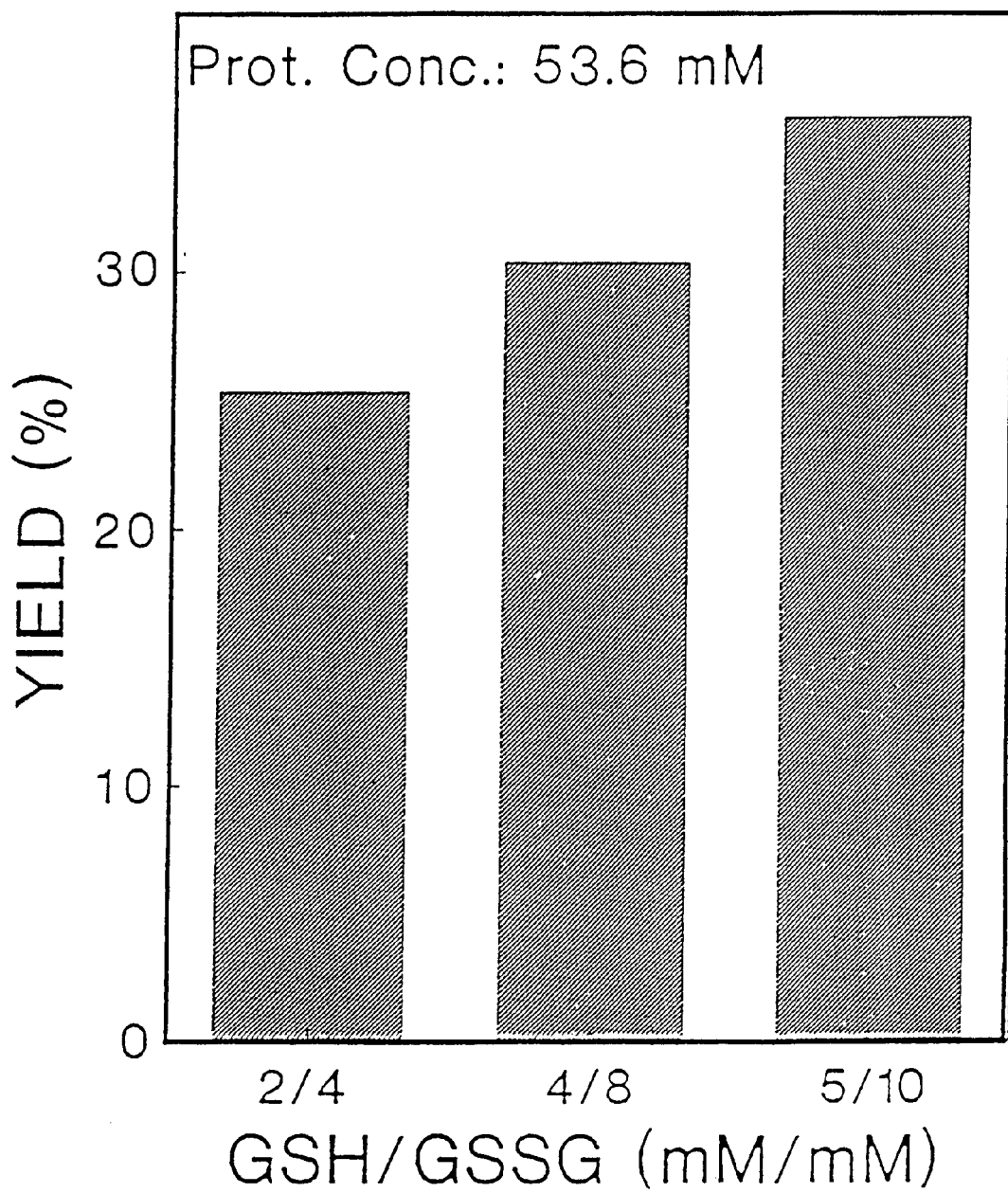

The following figures are attached:

FIGS. 1 and 2 illustrating yield depency in % on protein conc, Example 2b)

Figure 3:
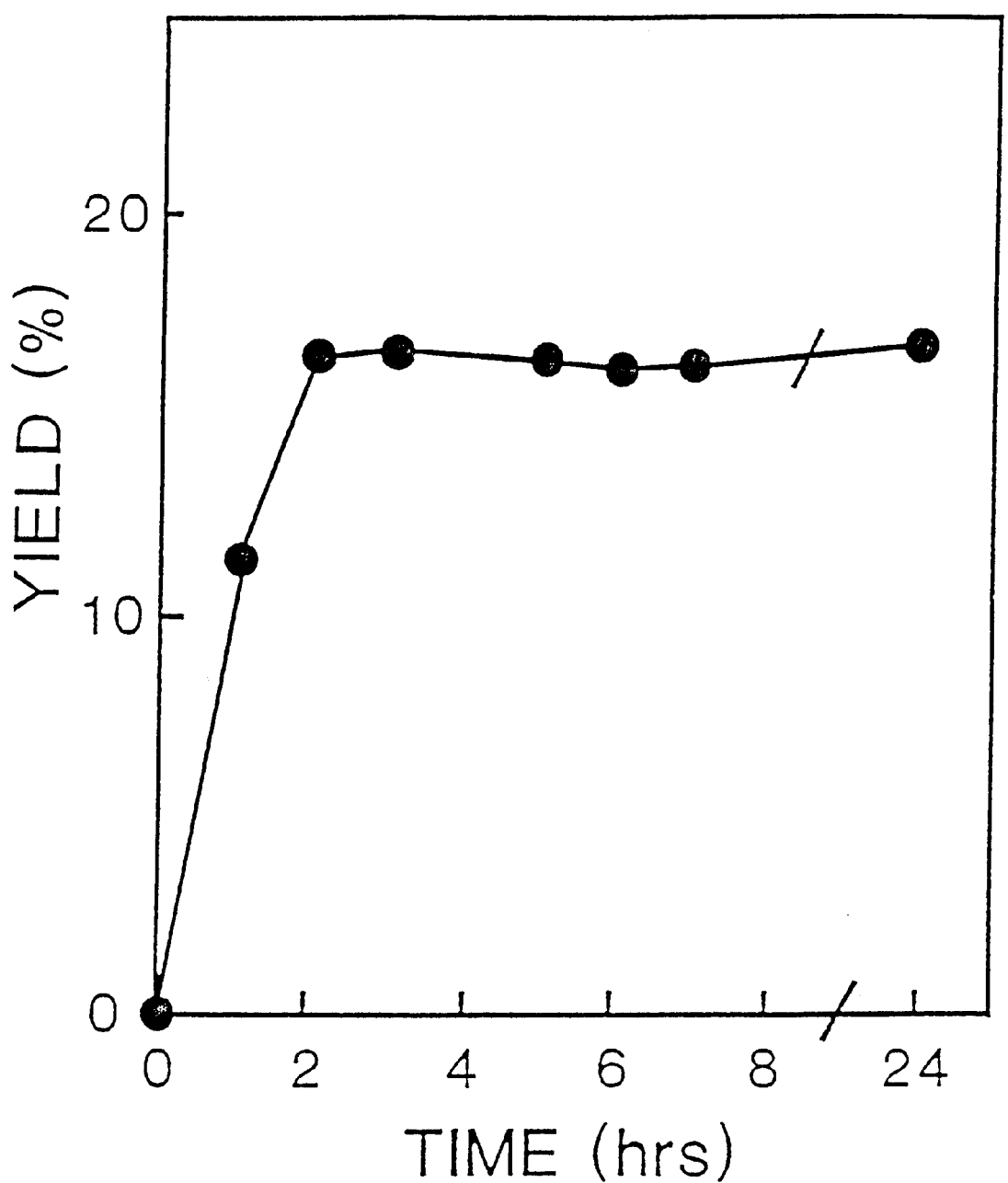

FIG. 3 illustrating kinetics of formation of ApoAI-M/ApoAI-M during 24 hours, Example 1 b2)

FIG. 4 illustrating synthetic linker, Example 3a)

Figure 5:
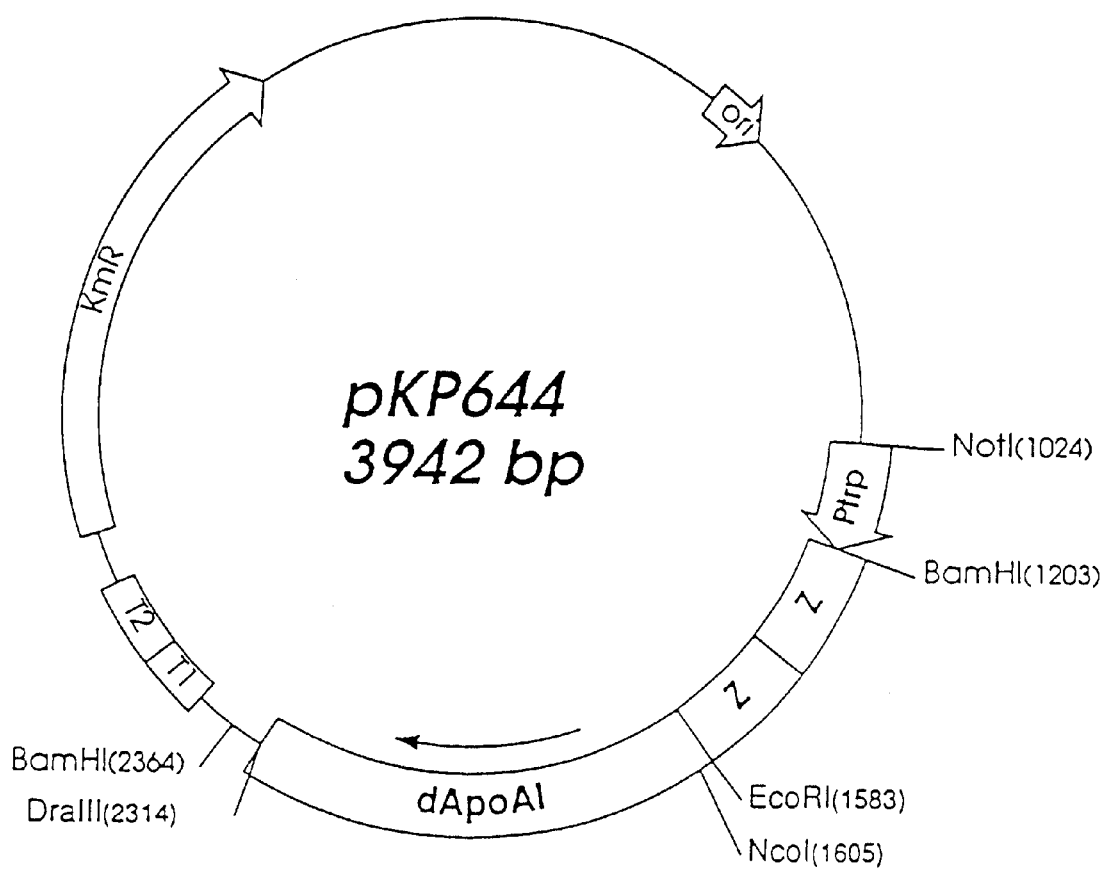

FIG. 5 illustrating plasmid, Example 3a).

FIGS. 6A and 6B illustrate Western analysis after cleavage of fusion protein, Example 3d)

Figure 7:
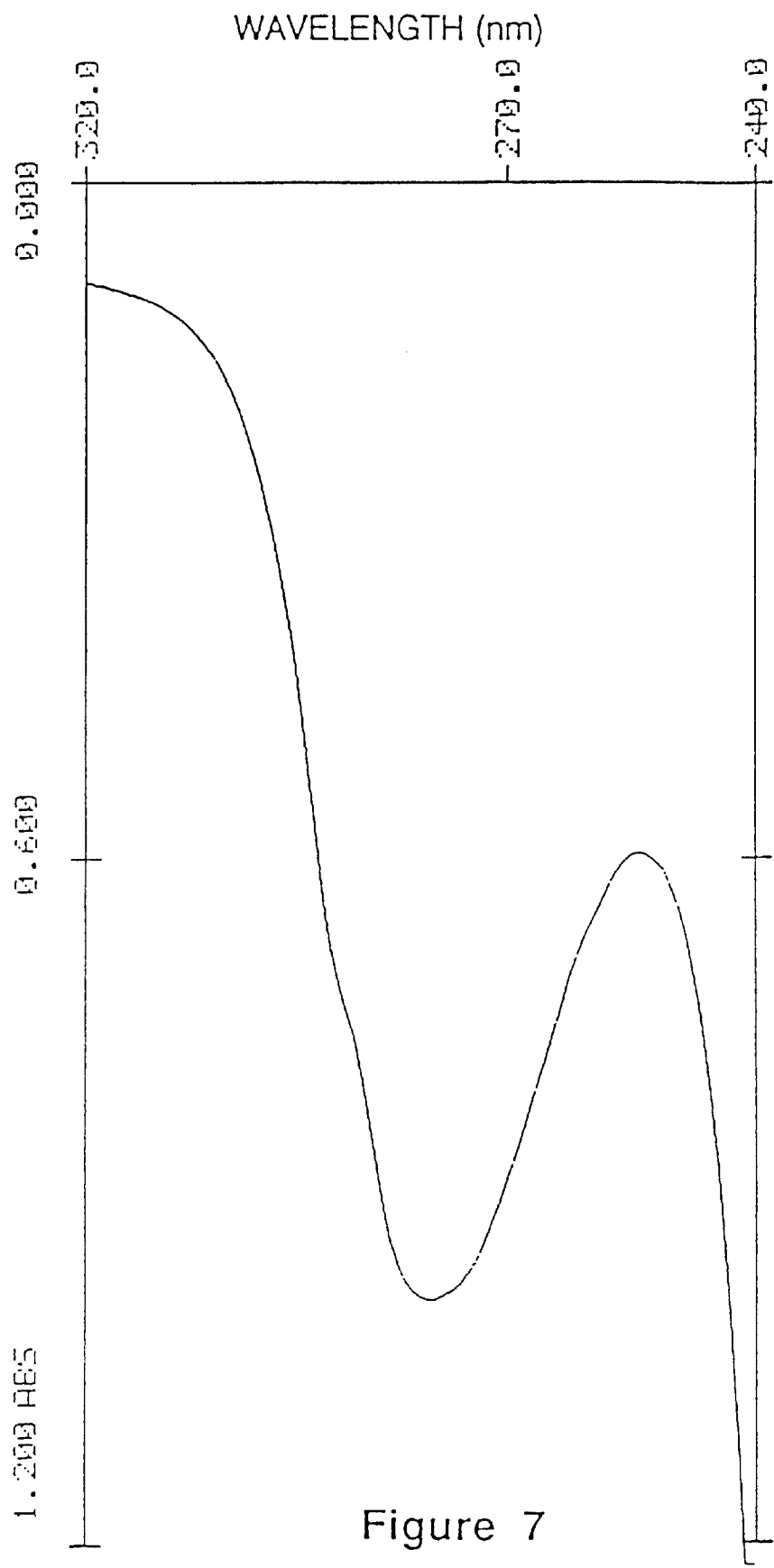

FIG. 7 illustrating UV spectrum of ApoAI-M/ApoAI-M, Example 5

Figure 8:
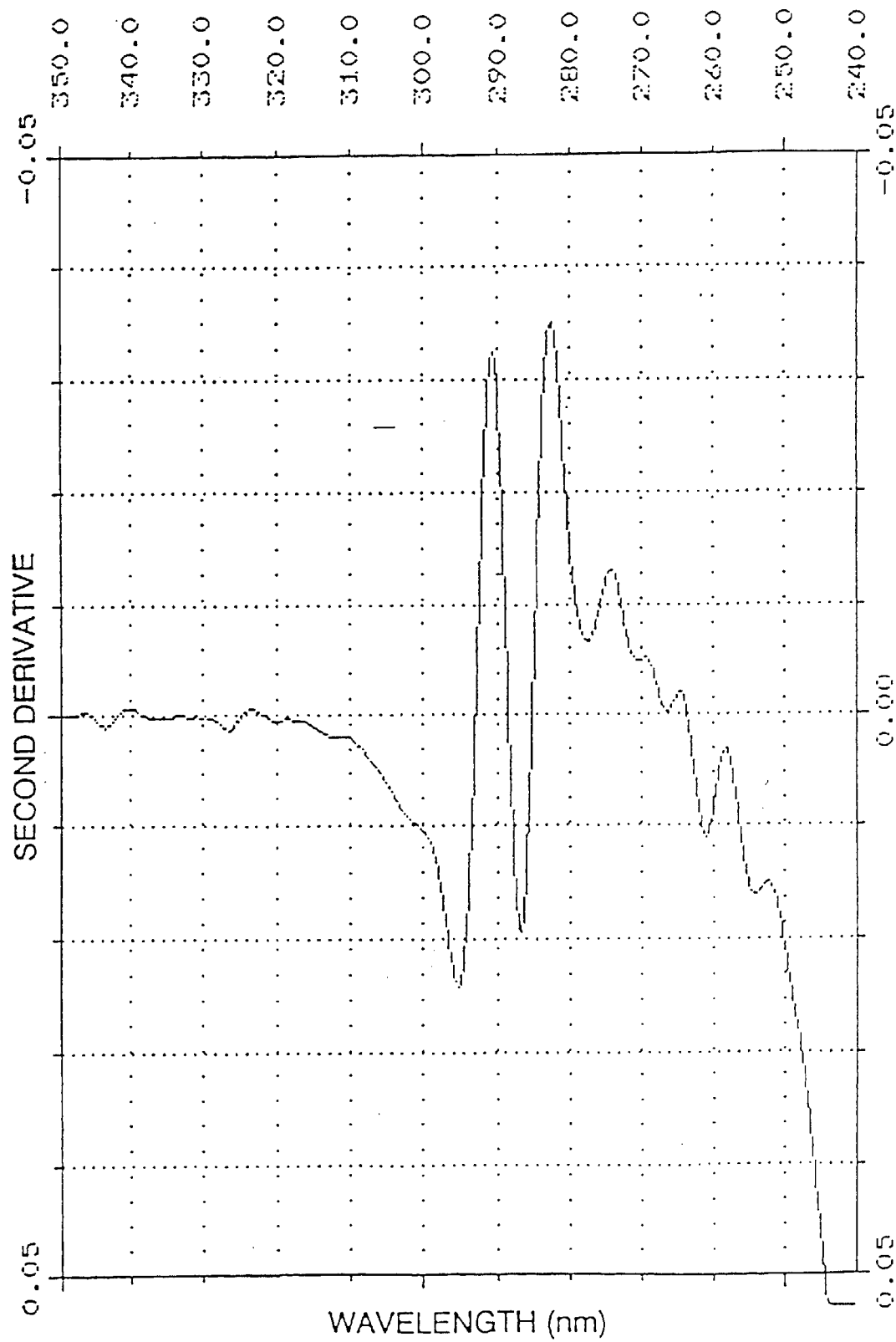
Figure 9:
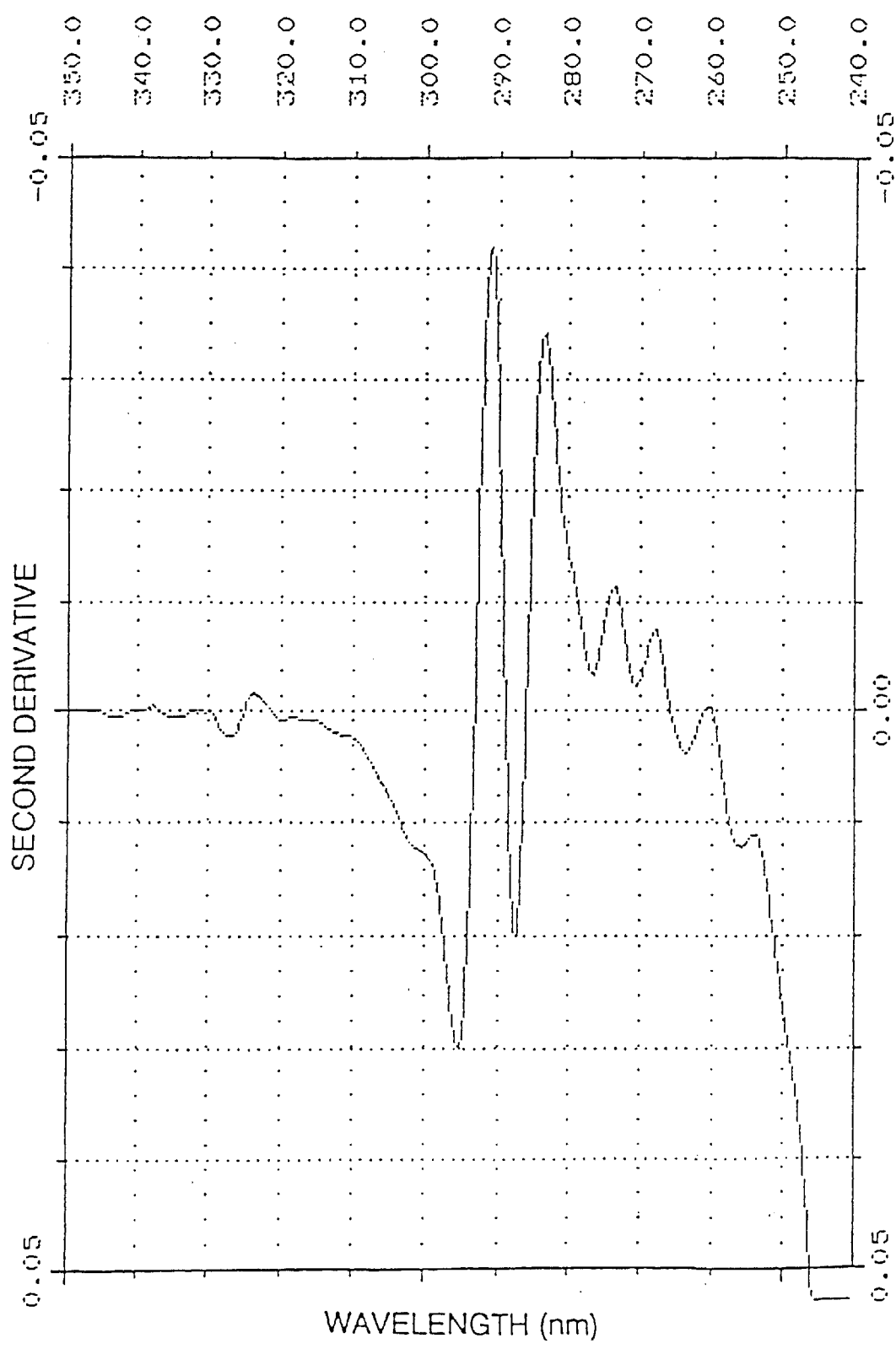
Figure 10:
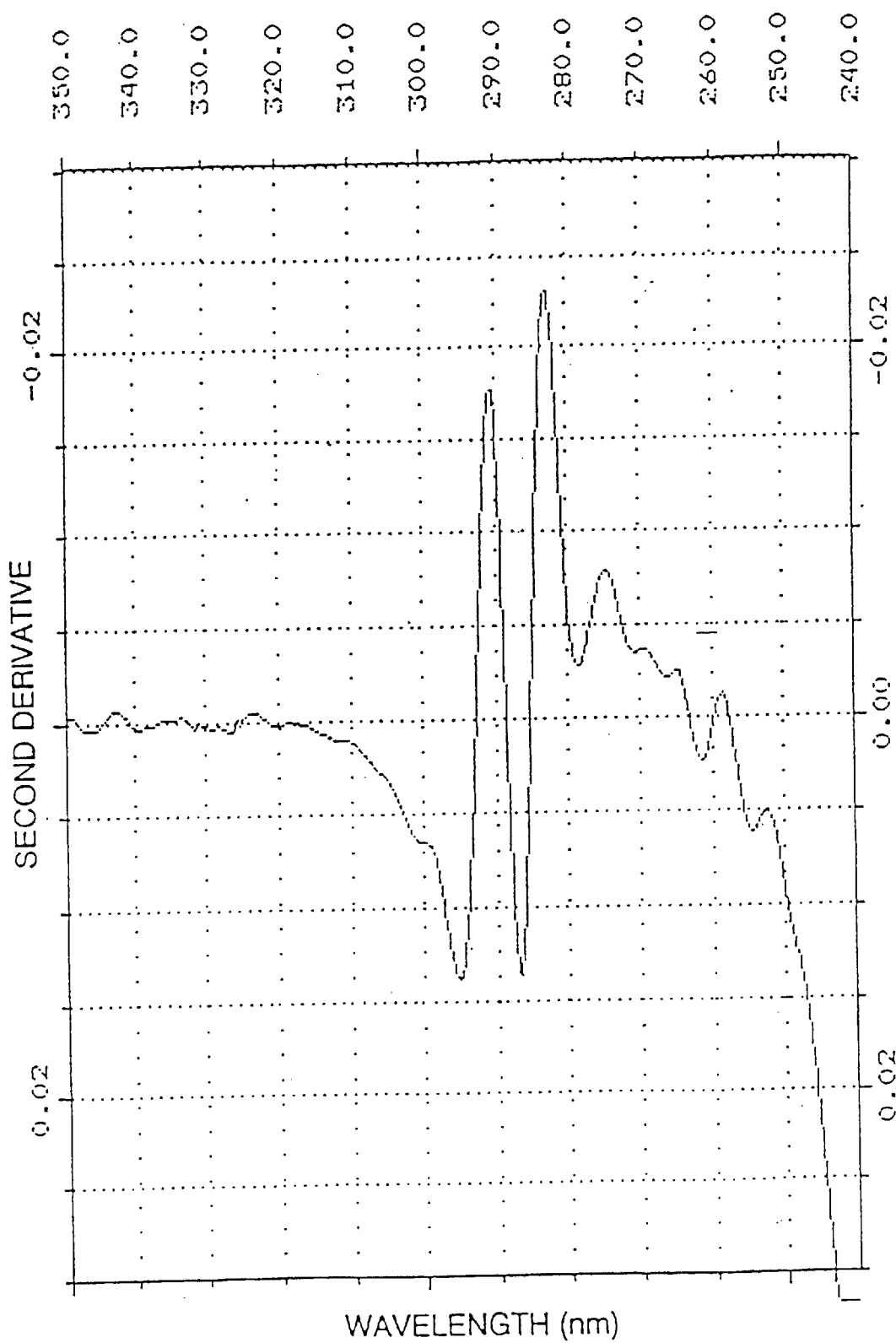

FIGS. 8–10 illustrating Second derivative UV spectra, Example 5

Figure 11:
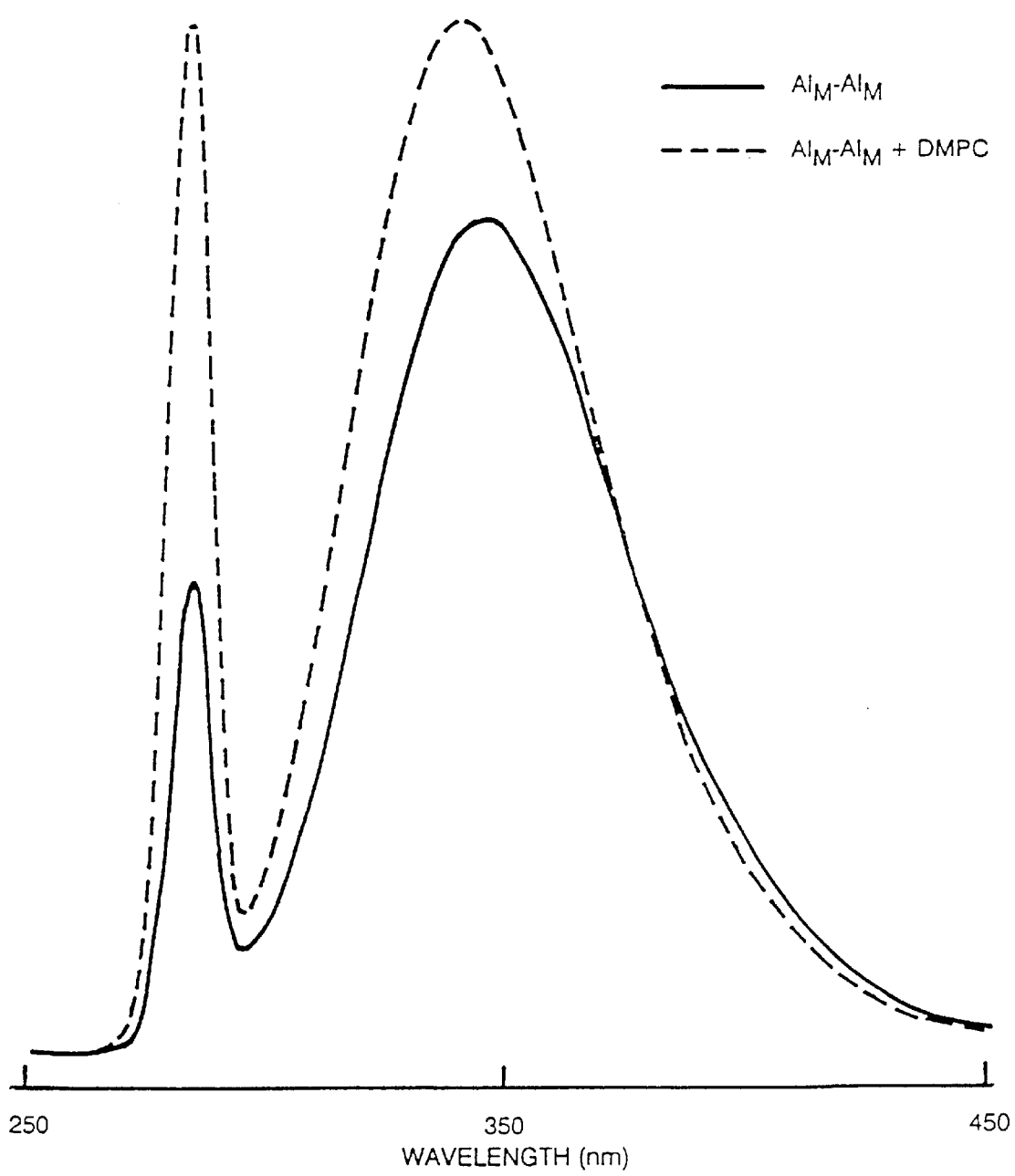

FIG. 11 illustrating Fluorescence spectroscopy, Example 5

Figure 12:
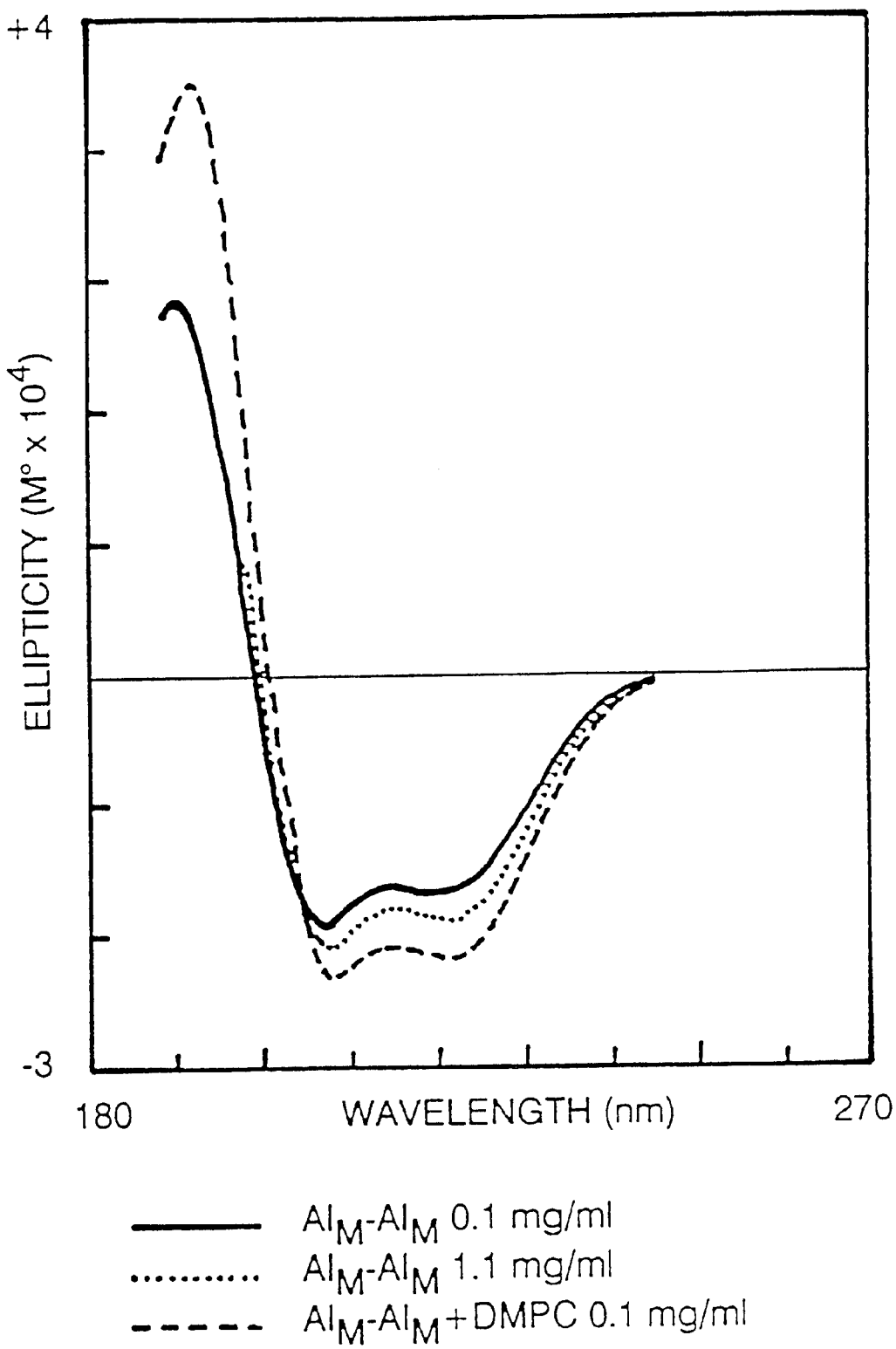

FIG. 12 illustrating CD spectroscopy, Example 5.

Figure 13:
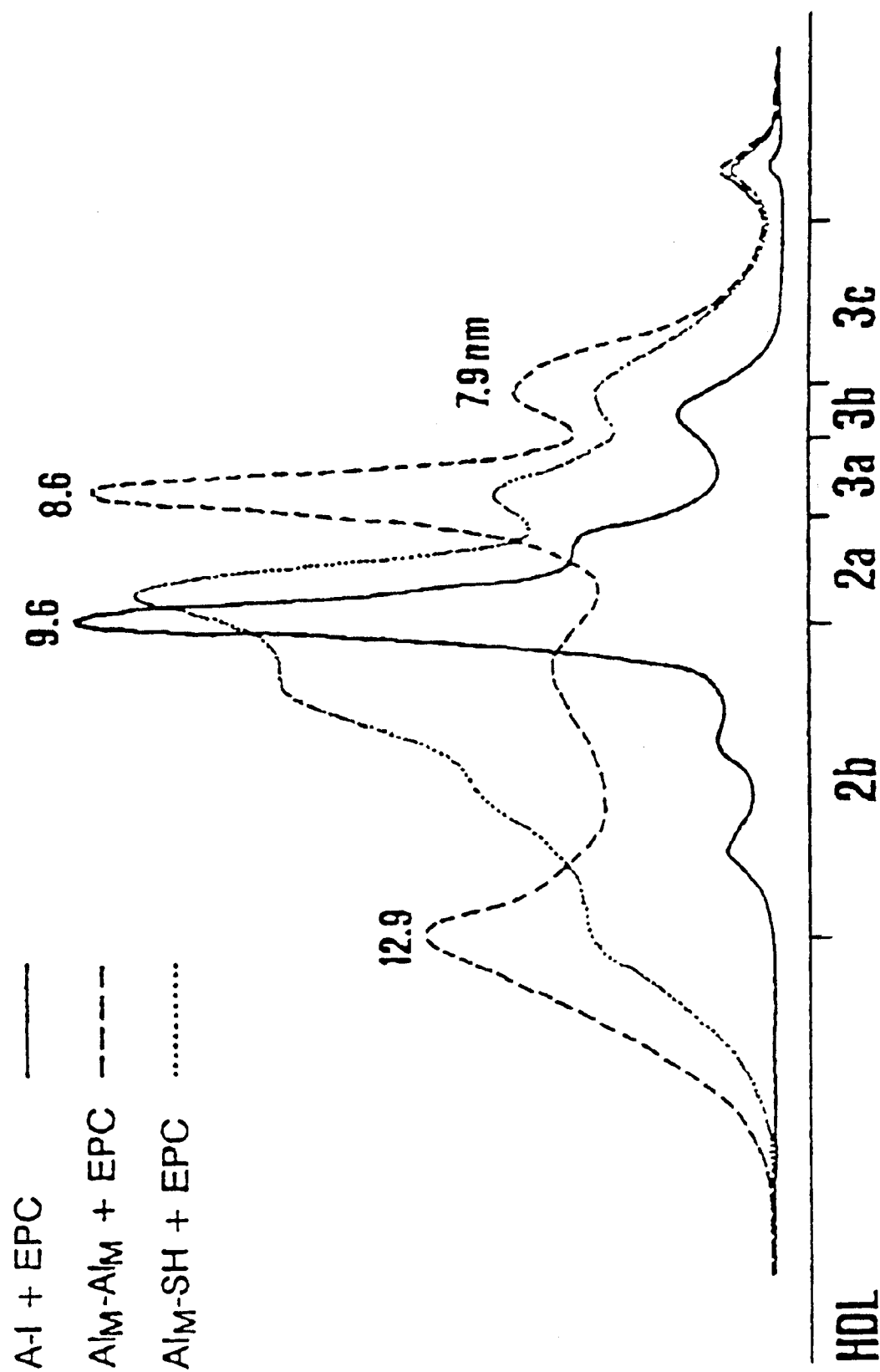

FIG. 13 illustrating rHDL containing ApoAI, ApoAI-M and Apo AI-M/ApoAI-M, Example 6.

EXPERIMENTAL

Example 1

Isolation of the Dimer From Plasma a) Preparation of Apolipoproteins

Fasting blood samples were collected on $Na_2$-EDTA (1 mg/ml) from different apolipoprotein ApoAI-M carriers, and plasma was prepared by low speed centrifugation at 4° C. Plasma high density lipoproteins (HDL, d=1.063–1.21 g/ml) were isolated by sequential ultracentrifugation (Havel R J, Eder H A, Bragdon J H. The distribution and chemical composition of ultracentrifugally separated lipoproteins in human serum. J Clin Invest 1955; 34:1345–1354) in a Beckman L5-50B ultracentrifuge equipped with a 50.2 Ti rotor. After a 48 h ultracentrifugation at 40,000 rpm at 4° C., the top fraction containing HDL was diluted 1:1 with a 0.15 M NaCl, 0.01% $Na_2$-EDTA, KBr solution (pH 7.4, d=1.21 g/ml) and recentrifuged at 40,000 rpm, 4° C. for 48 h. HDL were dialyzed exhaustively against 5 mM $NH_4HCO_3$, 0.01% $Na_2$-EDTA, pH 7.4, lyophilized and delipidated with diethylether/EtOH (3:1 v/v). Protein concentration was measured either by amino acid analysis or by the method of Lowry et al (Lowry O H, Rosenbrough N J, Farr A L, Randall R J. Protein measurement with the Folin phenol reagent. J Biol Chem 1951; 193:265–275)

b) Isolation of ApoAI-M/ApoAI-M

To isolate the ApoAI-M/ApoAI-M, HDL apolipoproteins from Example 1a) were solubilized in 0.1 M Tris-HCl, 0.04% $Na_2$-EDTA, 0.01% $NaN_3$, pH 7.4, containing 6M Guanidin HCl (Gdn-HCl). The apolipoproteins were applied to a Sephacryl S-300 HR column (2.6×300 cm) equilibrated with 0.1 M Tris-HCl, 0.04% $Na_2$-EDTA, 0.01% $NaN_3$, pH 7.4, containing 4 M Gdn-HCl. Apolipoproteins were eluted with the same buffer, at a flow rate of 1.5 ml/min; fractions of 10 ml were collected. Pooled fractions containing the ApoAI-M/ApoAI-M were concentrated under vacuum and reapplied to the same column.

The fractions containing the pure ApoAI-M/ApoAI-M were pooled, dialyzed against 5 mM $NH_4HCO_3$, 0.01% $Na_2$-EDTA, pH 7.4, lyophilized and stored at −20° C. in 0.1 M Tris-HCl, 0.04% $Na_2$-EDTA, 0.01% $NaN_3$, pH 7.4, containing 3 M Gdn-HCl. ApoAI-M/ApoAI-M preparations were >98% pure, as checked by high-performance size-exclusion chromatography (HPSEC) and SDS-polyacrylamide gel electrophoresis (SDS-PAGE) under non-reducing conditions.

By this method pure dimer of ApoAI-M has been isolated from plasma from carriers.

Example 2

Purification of the Monomer from Plasma and Conversion Thereafter to the Dimer a) Purification of ApoAI-M To purify the ApoAI-M monomer, HDL apolipoproteins from Example 1a) were solubilized in 0.1 M Tris-HCl, 0.04% $Na_2$-EDTA, 0.01% $NaN_3$, pH 7.4, containing 6M Gdn-HCl and 1% 2-mercaptoethanol. After 4 h of incubation at 37° C., reduced apo-HDL were applied to a Sephacryl S-200 column (2.6×150 cm) equilibrated with 0.1 M Tris-HCl, 0.04% $Na_2$-EDTA, 0.01% $NaN_3$, pH 7.4, containing 4 M Gdn-HCl and 0.1% 2-mercaptoethanol. Apolipoproteins were eluted with the same buffer, at a low rate of 1.0 ml/min; fractions of 5 ml were collected. Pooled fractions corresponding to apo AI+apo AI-M were dialyzed against 5 mM $NH_4HCO_3$, 0.01% $Na_2$-EDTA, pH 7.4 and lyophilized. Apolipoproteins were dissolved in 0.1 M Tris-HCl, 0.04% $Na_2$-EDTA, 0.01% $NaN_3$, pH 7.4, containing 6M Gdn-HCl and 1% 2-mercaptoethanol. After a 4 h incubation at 25° C., 2-mercaptoethanol was removed by Sephadex G25 chromatography and apolipoproteins immediately applied to a Thiopropyl-Sepharose. column. (1×10 cm) equilibrated with 0.1 M Tris-HCl, 0.04% $Na_2$-EDTA, 0.01% $NaN_3$, pH 7.4, containing 4 M Gdn-HCl. After an overnight recycling at a low flow rate (0.15 ml/min), normal ApoAI was eluted with 0.1 M Tris-HCl, 0.04% $Na_2$-EDTA, 0.01% $NaN_3$, pH 7.4, containing 4 M Gdn-HCl. ApoAI-M was then eluted with the same buffer containing 4 M Gdn-HCl and 1% 2-mercaptoethanol. Apo AI-M containing fractions were pooled, dialyzed against 5 mM $NH_4HCO_3$, 0.01% $Na_2$-EDTA, pH 7.4, lyophilized and stored at −20° C. in 0.1 M Tris-HCl, 0.04% $Na_2$-EDTA, 0.01% $NaN_3$, pH 7.4, containing 3 M Gdn-HCl and 0.1% 2-mercaptoethanol. ApoAI-M preparations were >98% pure, as checked by HPSEC, SDS-PAGE and isoelectric focussing.

b) ApoAI-M/ApoAI-M Synthesis

ApoAI-M solutions were dialyzed against 25 mM Tris-HCl buffer, pH 9.0. The reduced ApoAI-M was diluted to the desired final concentration (3.6–53.6 μM) with 25 mM Tris-HCl buffer containing reduced glutathione (GSH) (1–5 mM) and preincubated at 25° C. for 5 min. Oxidation was initiated by the addition of oxidized glutathione (GSSG) (0.1–10.0 mM) and proceeded in tightly closed tubes at the same temperature for 24 h. The oxidation was monitored by SDS-PAGE (see before). After staining and destaining, the gels were scanned with a LKB Ultroscan XL laser densitometer, and the percentage distribution of individual protein bands calculated with the LKB 2400 Gelscan XL software. The oxidation kinetics were monitored by HPSEC.

In order to optimize the synthesis of the dimer additional oxidation experiments were carried out in the presence of GSH/GSSG+Gdn-HCl and GSH/GSSG+thioredoxin. (Pigiet VP et al, Proc. Natl. Acad. Sci. USA 1986;83:7643–7647).

The oxidation of ApoAI-M was carried out in closed tubes, in the presence of variable concentrations of reduced/oxidized glutathione (GSH/GSSG). The reaction yield of the dimer was dependent both on protein concentration (FIG. 1 Table 1) and GSH/GSSG concentration/ratio (FIG. 2, Table 1). By increasing the protein concentration from 8.9 μM to 53.6 μM, the percentage of Apo AI-M/ApoAI-M increased by 26%–51% (FIG. 1, Table 1). A decrease in the GSH/GSSG molar ratio from 1/2 to 1/16 resulted in a 43% reduction of yield; on the other hand the rise in the GSH/GSSG concentration, with a constant GSH/GSSG molar ratio, was associated with an up to 42% increase in ApoAI-M/ApoAI-M formation (FIG. 2, Table 1). Both the reaction temperature and the presence of a protein denaturant (Gdn-HCl) did not affect the degree of ApoAI-M/ApoAI-M generation. A significant formation of ApoAI-M/ApoAI-M was also achieved by incubation of ApoAI-M with GSH/GSSG in the presence of 0.2 mM thioredoxin (Table 1).

The kinetics of the oxidation reaction were monitored by analytical HPSEC. The dimeric and monomeric apo AI-M gave distinct peaks with retention times of 10.8 and 12.7 min, respectively. The AI-M/AI-M synthesis (GSH/GSSG, 2 mM/4 mM, AI-M concentration 8.9 μM) was nearly completed after 3 h; a prolongation of the incubation up to 24 h did not further increase the AI-M/AI-M formation (FIG. 3).

TABLE 1

Apo Al-M oxidation

| Protein μM | GSH mM | GSSG mM | Yield % | Notes |
|---|---|---|---|---|
| 3.6 | 1.0 | 0.1 | 34.8 | thioredoxin 0.2 mM |
| 8.9 | 1.0 | 2.0 | 9.1 | |
| 8.9 | 1.0 | 2.0 | 9.9 | 4° C. |
| 8.9 | 1.0 | 4.0 | 7.2 | |
| 8.9 | 1.0 | 4.0 | 7.7 | 4° C. |
| 8.9 | 1.0 | 8.0 | 6.6 | |
| 8.9 | 1.0 | 16.0 | 5.2 | |
| 8.9 | 2.0 | 4.0 | 19.6 | |
| 8.9 | 4.0 | 8.0 | 18.7 | |
| 8.9 | 5.0 | 10.0 | 23.9 | |
| 8.9 | 1.0 | 2.0 | 9.8 | Gdn-HCl 4M |
| 17.9 | 2.0 | 4.0 | 23.3 | |
| 17.9 | 4.0 | 8.0 | 25.5 | |
| 17.9 | 5.0 | 10.0 | 27.5 | |
| 35.7 | 2.0 | 4.0 | 25.9 | |
| 35.7 | 4.0 | 8.0 | 27.7 | |
| 35.7 | 5.0 | 10.0 | 27.9 | |
| 53.6 | 2.0 | 4.0 | 25.4 | |
| 53.6 | 4.0 | 8.0 | 30.4 | |
| 53.6 | 5.0 | 10.0 | 36.1 | |

Reactions conditions:
Buffer: Tris-HCl 25 mM, pH 9.0
Temperature: 25° C.
Time: 24 hrs Example 3

Recombinant Production of ApoAI-M/ApoAI-M
a) Construction of the Expression Vector pKP644:

The Replicative Form of Bacteriophage M13mp18 containing the cDNA coding for the Apolipo protein AI-M (Sharpe C R et al, Nucleic Acids Research, Vol 12, No 9, p 3917. 1984 and Cheung M C et al, Biochem Biophys Acta 960, pp 73–82, 1988) was digested with the restriction enzyme BamHi and purified by Low Gelling Temperature (LGT) agarose gel electrophoresis. The 822 bp fragment corresponding to the ApoAI-M gene was excised and ligated to the plasmid pUC9, previously digested with BamHI and treated with Calf Intestinal Phosphodiesterase.

The ligation mixture was used to transform competent E.coli JM83 and white colonies were picked from agar plates containing Ampicillin, X-Gal and IPTG. Plasmid-DNA was prepared and purified on QuiaGene columns, (QuiaGene Inc, 9259 Eton ave., Chatsworth, Calif. 91311 USA) according to the manufacture's recommendations. The derived plasmid, denominated pUC/ApoAI-M was digested with EcoRI and NcoI. An aliquot of the digestion mixture was analyzed by agarose electrophoresis to confirm the correct orientation. Another aliquot was used to ligate the synthetic linker "ΔApoAI-Eco" (FIG. 4) to the 5'-end of the ApoAI-M gene in order to generate the gene ΔApoAI, consisting of 724 bp. The ΔApoAI-M sequence generates an Asp-Pro site at the N terminal of the encoded protein which facilitates cleavage by formic acid. Competent E.Coli JM83 were transformed with the ligation mixture and the derived plasmid (denominated pUC/ΔApoAI-M) was isolated on QuiaGene columns as above.

The plasmid pUC/ΔApoAI-M and the expression vector pEZZ was digested with EcoRI and BamHI, purified by LGT agarose electrophoresis and the 799 bp fragment of pUC/ΔApoAI-M was ligated to the 2763 bp fragment pf pEZZ. The ligation mixture was used to transform competent E.coli RV308 and plasmid DNA was prepared as above.

For the experimental procedures see Sambrook J., Fritsch E. F. and Maniatis T. (1989) Molecular Clonings; A laboratory Manual, 2nd edit. Cold Spring Harbor Laboratory, Cold Spring Harbor, N.Y.

The derived plasmid was denominated pKP644. (FIG. 5)
b) Expression of the Fused Protein ZZ-ΔApoAI-M.

Figure 6:
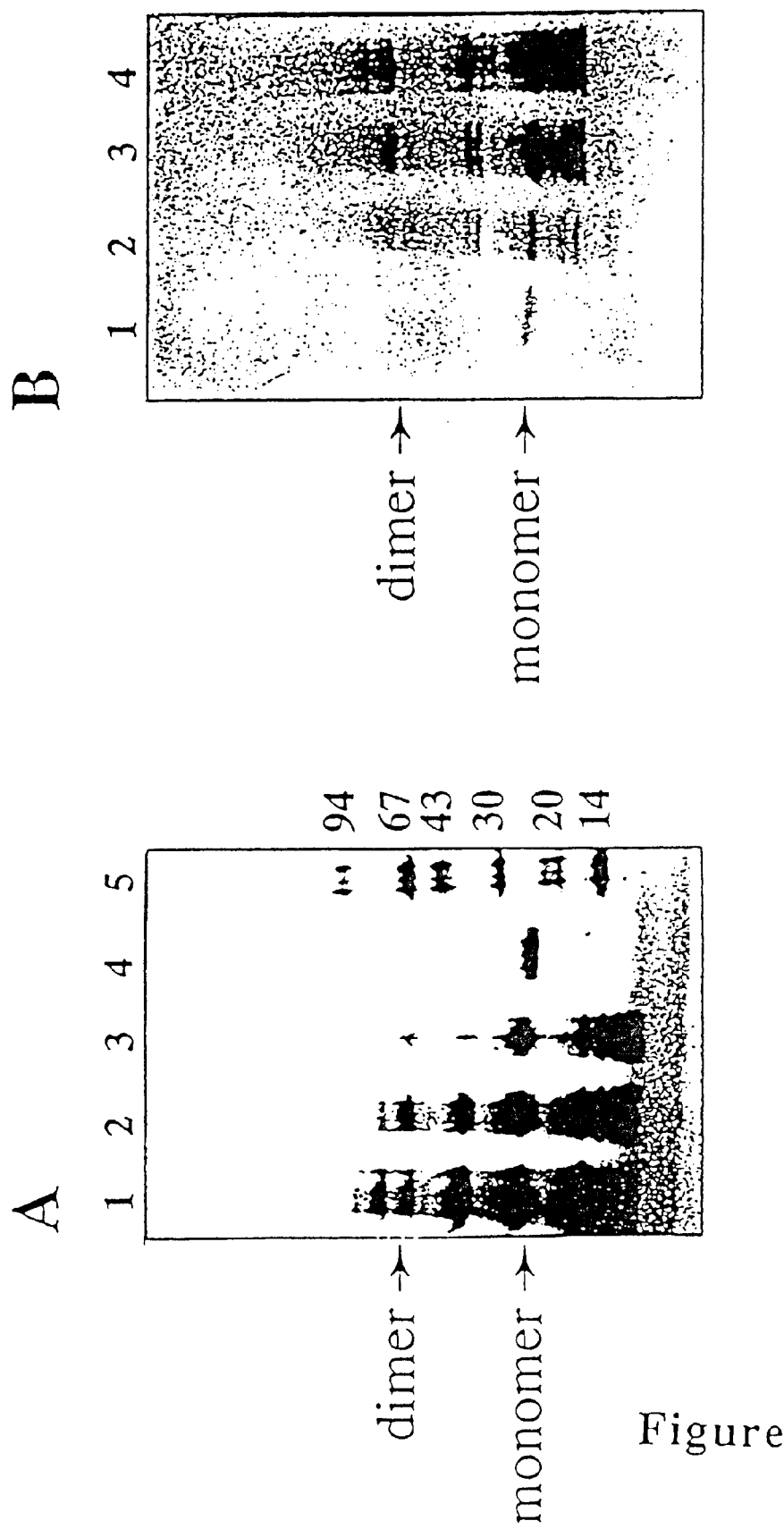

40 ml of an overnight culture of E.Coli RV308/pKP644, grown at 30° in LB with 50 mg/ml Kanamycin, was inoculated in 2×500 ml minimal medium A (Curr. Meth. in Mol. Biol) with addition of 0.2 g/l Casamino Acids, 1 mM MgSO$_4$, 0.25% Glucose and 50 mg/ml Kanamycin. The culture was incubated at 37° for 24 hours under vigorous shaking.

c) Initial Purification of ApoAI-M 1.0 l of an E. coli culture (RV308/pKP644) containing the described plasmid was centrifuged and the pelleted cells resuspended in 30 ml of 1×TS (25 mM Tris HCl, 0,2 M NaCl, 1 mM EDTA) and 6M GdnHCl and homogenized by a single passage through a French Press (SLM Instruments Inc.) at a working pressure of 1000 psi. The resulting suspension was incubated at room temperature with gentle shaking for 1 h and centrifuged. The supernatant was then diluted to a final concentration of GdnHCl of 1M (i.e. six times) and loaded onto a column of 15 ml Sepharose FastFlow IgG equilibrated with 1×TS. After loading, the column was washed with 5 column volumes of 1×TS followed by 20 mM ammonium acetate pH 5.4 until the pH of the eluate reached 5.4. The bound material was eluted with 25 ml of 0.2 M HAc and the absorbance at 280nm (A$_{280}$) was monitored. The yield from a 1 L culture was 1.9 mg based on the A$_{280}$-value.

d) Cleavage of the Fusion Protein:

The eluate was aliquoted, lyophilized and resuspended in 75%, 50% and 25% formic acid respectively. The solutions were incubated at 37° C. for 28 h and thereafter lyophilized to remove the formic acid. The cleavage products were assayed using SDS-PAGE followed by a Western analysis. Approximately 5 mg of total protein was loaded onto SDS-PAGE gel gradient 8–25% under non-reducing conditions. The samples were run in duplicate. One gel was stained with Coomassie and one used for Western analysis. The results are shown in FIG. 6. One of the cleavage products comigrates with the purified native ApoAI and gives rise to a signal in the Western analysis. Western analysis was performed using polyclonal antibodies conjugated with horseradish peroxidase (The Binding site Ltd; Cambridge, England) and visualized using standard procedures.

FIG. 6 shows the analysis of the resulting proteins after cleavage of the fusion protein. Panel A; Coomassie stained SDS-PAGE gel (8–25%). Lane 1: 25% formic acid, lane 2: 50% formic acid; lane 3: 75% formic acid; lane 4: Purified native ApoAI (Sigma) and lane 5: LMW marker (Pharmacia). Panel B: Western analysis of a duplicate gel. Lane1: Purified native ApoAI (Sigma); lane 2: 75% formic acid, lane 3: 50% formic acid and lane 4: 25% formic acid. The presence of a band at twice the molecular weight of ApoAI-M on the Western analysis showed that the dimers of ApoAI-M were present.

Example: 4

Production of ApoAI-M in Bioreactors

Construction of Vectors for Direct Secretion of ApoAI-M to the Periplasmic Space and Growth Medium Strains and Vectors. The *Escherichia coli* K12 strains used were HB101 F$^-$, hsd S20(rB$^-$, mB$^-$) supE44. HB101 F$^-$, hsd S20(rB$^-$, mB$^-$), supE44, ara14, I$^-$, galK2, lacY1), proA2, rspL20, xyl-5, mtl-1, recA13, rB$^-$, mB$^-$, mcrA(+), mcrB(−) (Boyer et al,. 1969. J Mol Biol 41:459–472), DH5a F$^-$, F80D1acZDM15, D(lacZYA-argF)U169, recAI, endAI, gyrA, I$^-$, thi-I, hsdR17, (rk$^-$, mk$^+$), supE44, relAI, (BRL USA). RV308 DlacX74, galOP::lS2(galOP308), strA, I$^-$. (Maurer et al,. 1980. J Mol Biol. 139:147–161) and BC50 xyl-7, ara-14, T4-R, I$^-$. The strains HB101 and DH5a were used for subcolning of DNA fragments. The plasmid pUC9 (Vieira et al, 1982. Gene 19:259–68) was used for subcloning of a 821 bp BamHI fragment of a cDNA copy of human ApoAI obtained from S. Sidoli (Milano). The nucleotide sequence of human ApoAI cDNA kan be obtained from GenBank under the accession number X02162. (Seilhammer et al. 1984. DNA 3:309–317). This vector was designated pKP575. Also a 856 bp EcoRI-PstI fragment of human ApoAI-M DNA, (cDNA copy obtained from S. Sidoli), was subcloned into the plasmid pUC9. This derivative was designated pKP576. The plasmids pKP683 and pKP764 are derivatives of the plasmids pTrc 99 (Amann et al. 1988. Gene. 69:301–15) and a pUC derivative with the transposon (Tn903) derived kanamycin resistance marker from pUC4-K (Vieira et al 1982. Gene 19:259–268 and Oka et al, 1981. J Mol Biol 147:217) and the transcription terminators (T1T2) of the bacteriophage fd, from pUEX2, (Bressan et al, 1987. Nucleic Acid. Res. 15:10056)

Methods Employed. The bacterial strains were grown in Luria Bertani medium (LB) or yeast tryptone medium (2×YT) with ampicillin (Ap) 50 μg/ml or kanamycin (Km) 70 μg/ml for preparation of plasmid DNA and for small scale expression analysis (Sambrook et al, 1989. Cold Spring Harbor Laboratory Press). Tryptose blood agar base (Difco, USA), supplemented with Ap 50 μg/m or Km 70 μg/ml, were used for growing cells on agar plates. Recombinant DNA techniques were performed according to (Sambrook et al,. 1989. Cold Spring Harbor Laboratory Press). Restriction endonucleases and T4 DNA ligase were obtained from Boehringer Mannheim (Germany), New England Biolabs (Beverly, USA) or Pharmacia (Uppsala, Sweden). Isopropyl-b-D-galactoside (IPTG) was obtained from Sigma (USA). Low gelling and melting temperature agarose (NuSieve GTG, FMC Bioproducts, USA) was used to isolate DNA fragments. The PCR amplifications were performed using the DNA thermal cycler and Taq DNA polymerase from Perkin-Elmer/Cetus Instruments (Norwalk, USA). Oligonucleotide linkers and primers were synthesized on a Pharmacia-LKB Gene Assembler Plus from Pharmacia (Uppsala, Sweden) using the phosphite triester method on solid phase. The nucleotide sequence determination was performed on an Applied Biosystem 373A DNA sequencer, using the Taq DyeDeoxy™ Terminator Cycle Sequencing Kit from Applied Biosystem (USA).

DNA computer programs used. The Macintosh program PlasmidARTIST (version 1.2) (Clontech, USA) was used for drawing the plasmid maps and the GCG Sequence Analysis Software Package (Genetics Computer Group, Inc, Madison Wis. USA) was used for handling DNA sequences on Digital VAX computers.

Construction, Expression and Secretion of ApoAI-M in Bacteria. The aim of the vector constructions was to obtain a production secretion system for ApoAI-M in *E. coli* with a very high level of ApoAI-M secreted into the growth medium.

Two oligonucleotides were synthesized for fusing the ApoAI and ApoAI-M cDNA copies to DNA fragments encoding bacterial signal sequences. The 14 bp EcoRI and NcoI fragment and the 40 bp NcoI fragment of pKP575 was replaced by a synthetic 37 bp EcoRI NcoI fragment into a plasmid designated pKP580. The BbsI cleavage site in this synthetic DNA fragment gives the same cleavage site as MluI, which facilitates cloning of different fragments encoding bacterial signal sequences. The plasmid pKP631 was constructed by replacing a 702 bp NcoI-DraIII fragment of pKP575 (ApoAI) by a 702 bp NcoI-DraIII fragment of pKP576 (ApoAI-M). From the plasmid pKP631 a 820 bp BbsI-HindIII fragment was isolated and inserted at the MluI and HindIII of a plasmid vector that was designated pKP682 This vector contains a tac-promoter (Ptac), a derivative of an ompA signal sequence, two transcription terminators and a kanamycin resistance marker. A 1501 bp NruI-NruI fragment was isolated from pKP682 and was inserted into a similar vector but with the Ptac replaced by the Ptrc promoter. This expression vector was designated-pKP683. The plasmid pKP764 was constructed by replacing the 88 bp DraIII-HindIII of pKP683 by a 14 bp synthetic DNA fragment, containing stronger translation terminators and destroying the DraIII site by the introduction of an A at the end of the DraIII overhanging 3' end. Transformation of *E. coli* strains were performed as described in (Sambrooket al, 1989. Cold Spring Harbor Laboratory Press). The plasmid constructions used for expression experiments and for production of ApoAI-M was analysed using restriction enzyme mapping and the structural gene of ApoAI-M was confirmed by nucleotide sequence determination. The *E. coli* strains with the appropriate plasmids used for growth in bioreactors were prepared as follows. Cells were grown overnight in LB or 2×YT supplemented with Km in shake flasks at 30° C. After centrifugation the cell were resuspended in 1/2 volume of deep freeze storage medium according to Gergen et al, 1979. Nucleic Acid Res 7:2115. Aliquots were dispensed into 1 ml cryovials and stored at −75° C. untill used.

Growth mediums for cells grown in bioreactors. Medium A: 16 g/l tryptone (Difco, USA), 8 g/l yeast extract (Difco, USA), 5 g/l NaCl, and 0.05 g/l kanamycin. Medium B: 2.5 g/l $(NH_4)_2SO_4$, 3 g/l $KH_2PO_4$, 2 g/l $K_2HPO_4$, 0.5 g/l $Na_3$-citrate, 5 g/l yeast extract (Difco, USA). After sterilization the medium was supplemented with: 10 g/l initial. glucose, −0.05 g/l kanamycin, 1 g/l $MgSO_4 \times 7$ $H_2O$ and 0.07 g/l thiamine hydrochloride. A trace element solution (1 ml/l) and a vitamin solution (0.65 ml/l) were added. The trace element solution contained: 27 g/l $FeCl_3 \times 6$ $H_2O$, 4 g/l $ZnSO_4 \times 7$ $H_2O$, 7 g/l $COCl_2 \times 6$ $H_2O$, 7 g/l $Na_2MoO_4 \times 2$ $H_2O$, 8 g/l $CuSO_4 \times 5$ $H_2O$, 2 g/l $H_3BO_3$, 5 g/l $MnSO_4 \times 4$ $H_2O$, 11 g/l $CaCl_2 \times 2$ $H_2O$ and 50 ml/l HCl. The vitamin solution contained: 0.5 g/l calcium pantothenate, 0.5 g/l choline chloride, 0.5 g/l folic acid, 1 g/l inositol, 0.5 g/l nicotinamide, 0.5 g/l pyridoxine hydrochloride, 0.05 g/l riboflavin and 0.5 g/l thiamine hydrochloride. Adecanol (0.2 ml/l) was used as anti-foam. When necessary, further additions of anti-foam was made during the cultivation.

Cultivation of RV308/pKP683 in a bioreactor of 3.5 liters. Deep frozen stock culture was used to inoculate 500 ml medium A and precultivated in 2 l baffled Erlenmeyer flasks at 30° C. for 8–10 hrs. An inoculum volume corresponding to 10% of the bioreactor working volume was transferred to the bioreactor. The cultivation was performed in a bioreactor of 3.5 liters (Belach AB, Sweden) with a working volume of 2.5 liters. The temperature was 30° C. during the growth phase before induction and then raised to 37° C. The pH was maintained at 7.0 with a solution of 25% ammonia. The aeration rate was held at 1 vvm and the dissolved oxygen tension (D.O.T.) was kept at 30% by adjusting the impeller speed. After the initial glucose was consumed, a glucose fed-batch was initiated, keeping the system at glucose limitation by feeding a 60% solution of glucose. The initial feed rate, 0.04 g/min was kept for 3 hrs and then gradually increased to 0.4 g/min during 3 hrs. Cell growth was monitored by following the optical density (OD). The concentration of ApoAI-M in the supernatant was determined by radioimmunoassay (Apolipoprotein AI RIA 100 kit, art.no. 109152-01. Kabi Pharmacia, Sweden). After 16 hrs of cultivation, at an OD of 58, protein synthesis was induced by adding 0.5 mM IPTG and the temperature was increased to 37° C. Four hours after the induction the concentration of ApoAI-M was 2.3 g/l and after additional 2 hrs the concentration was 2.5 g/l.

Cultivation of BC50/pKP764 in a bioreactor of 3.5 liters. The cultivation was carried out as described above, except that no kanamycin was added to the bioreactor medium. After 15 hrs, at an OD of 60, IPTG was added and the temperature was raised. 10 hrs later the concentration of ApoAI-M in the supernatant was 3.7 g/l and 22 hrs after induction, the concentration was 4.4 g/l.

Cultivation of BC50/pKP764 in a bioreactor of 300 liters. A bioreactor of 300 liters (Chemoferm AB, Sweden) with a working volume of 180 liters was used. The inoculum was prepared as described above for growth of RV308/pKP683 in a bioractor of 3.5 liters, except that the precultivation time in shake flasks was 14 hrs. The inoculum was transferred to a 50 liters seed bioreactor with a working volume of 18 liters The medium used in the shake flasks as well as in the bioreactor was medium A. The seed bioreactor medium was supplemented with 5 g/l of glucose and the temperature was 30° C. The pH and aeration were as described above for growth of RV308/pKP683 in a bioractor of 3.5 liters and the D.O.T. was never below 30%. When the culture reached an OD of 4, the content of the seed bioreactor was transferred to the bioreactor of 300 liters. In this bioreactor the temperature, pH and aeration of the medium were as described above for growth of RV308/pKP683 in a bioractor of 3.5 liters. Before induction the D.O.T. was kept at or above 30% by increasing the impeller speed up to its maximum and thereafter increasing the air pressure. After induction the air pressure was increased to 2 bar resulting in a D.O.T. of 15–20%. After 16 hrs of cultivation in the bioreactor when the culture had an OD of 51, IPTG was added and the temperature was increased to 37° C.

The concentration of ApoAI-M as monomer and dimer was 1.3 g/l, 5 hrs after induction and during the following hour, while the bioreactor was cooled, the concentration of ApoAI-M increased to 1.5 g/l.

Any monomer present was converted to dimer and purified according to convetional methods.

Example 5

Characterization of ApoAI-M/ApoAI-M From Plasma

The purified ApoAI-M/ApoAI-M from Example 1 gave a single band in overloaded, non-reduced SDS-PAGE gels. In analytical SDS-PAGE, the apparent molecular weight of the protein was, as expected, 56 kD. Apo AI-M/ApoAI-M showed a complex isoform pattern, characterized by the presence of at least 6 different protein bands, in the 5.3–5.6 pI range, in nonreduced, denatured IEF gels.

The ApoAI-M/ApoAI-M (1.1 mg/ml) UV spectrum showed a typical absorbance maximum at 280 nm, with a shoulder at 290.2 nm (FIG. 7). The calculated protein E (1 cm, 1%) at 280 nm was 16.9. To evaluate the exposure of tyrosine residues in the ApoAI-M/ApoAI-M, a second-derivative analysis of UV spectra was carried out as described by Ragone R et al. Determination of tyrosine exposure in proteins by second-derivative spectroscopy. Biochemistry 1984; 23: 1871–1875. Second-derivative UV spectra typically showed two minima centered around 283 and 290.5 nm, and two maxima around 287 and 295 nm (FIGS. 8–10). The relative degrees of tyrosine exposure (alfa) calculated for the native ApoAI-M/ApoAI-M and ApoAI-M/ApoAI-M+DMPC were 0.75 and 0.49, respectively (Table 2).

TABLE 2

Characteristics of the APO Al-M/Apo Al-M protein

|  | Apo Al-M/Apo Al-M | Apo Al-M/Apo Al-M + DMPC |
|---|---|---|
| Molecular weight (kD) | 56.0 | |
| Isoelectric point | 5.3–5.6[1] | |
| UV Spectroscopy: | | |
| E (1 cm, 1%) | 16.9[2] | |
| Tyrosine exposure (alpha) | 0.75[2] | 0.49[2] |
| Fluorescence Spectroscopy: | | |
| Exc wavelength max(nm) | 280 | 280 |
| Em wavelength max(nm) | 344 | 338 |

TABLE 2-continued

Characteristics of the APO Al-M/Apo Al-M protein

| | Apo Al-M/Apo Al-M | Apo Al-M/Apo Al-M + DMPC |
|---|---|---|
| CD Spectroscopy | | |
| alpha-helix % | 52.2[3] 57.8[4] | 66.1[3] |

[1]at least 6 isoforms in denatured IEF gels
[2]a high value indicates an increased tyrosine exposure
[3]protein concentration: 0.1 mg/ml
[4]protein concentration: 1.1 mg/ml Both ApoAI-M/ApoAI-M (0.1 mg/ml) excitation and emission fluorescence spectra were recorded. The excitation wavelength maximum of tryptophanyl residues in ApoAI-M/ApoAI-M was at 280 nm, and did not change following association with DMPC. The emission spectrum (excitation at 280 nm) showed a 344 nm wavelength maximum (FIG. 11); the association with DMPC induced a shift toward the blue of this maximum (338 nm), associated with a 24% increase in flourescence intensity at the maxima (FIG. 11).

The ApoAI-M/ApoAI-M far-UV CD spectrum was characterized by typical minima at 208 nm and 222 nm and a maximum around 195 nm (FIG. 12). The alpha-helical content increased significantly with increasing protein concentrations from 0.1 mg/ml to 1.1 mg/ml (FIG. 12, Table 2). The association of ApoAI-M/ApoAI-M (0.1 mg/ml) with DMPC induced a further rise in the protein alpha-helical structure (FIG. 12, Table 2).

METHODS FOR THE CHARACTERIZATION OF THE PRODUCT

Incubation With Phosoholipids

Weighed amounts of dimyristoylphosphatidylcholine (DMPC) were dissolved in ethanol and the solvent evaporated under $N_2$; any remaining solvent was removed under vacuum for 2 h. Dispersions of DMPC in 20 mM phosphate buffer, pH 7.4 were mixed with Apo AI-M/ApoAI-M (0.1 mg/ml final) at a 100:1 DMPC/ApoAI-M/ApoAI-M molar ratio.

Spectroscopy

ApoAI-M/ApoAI-M solutions were dialyzed against 20 mM phosphate buffer, pH 7.4 and diluted with the same buffer to the desired protein concentration.

Normal and second-derivative UV spectra of ApoAI-M/ApoAI-M and ApoAI-M/ApoAI-M+DMPC solutions were recorded with Jasco Uvidec-610 and Perkin Elmer Lambda-2 spectrometers at 25° C., using a 1 cm quartz cell. Topographical location of tyrosine residues was investigated according to the equation of Ragone et al, (Ragone R, Colonna G, Balestrieri C, Servillo L, Irace G. Determination of tyrosine exposure in proteins by second-derivative spectroscopy. Biochemistry 1984; 23:1871–1875):

$$\text{alpha} = (r_n - r_a)/(r_u - r_a)$$

where alpha is the degree of tyrosine exposure to the solvent, $r_n$ and $r_u$ are the derivative peak ratios (a/b) for the native and unfolded (in 6M Gdn-HCl) ApoAI-M/ApoAI-M, respectively, and $r_a$ is the second derivative peak ratio of a solution containing free tyrosine and tryptophan mixed in the same molar ratio as that in ApoAI-M/Apo AI-M.

Intrinsic fluorescence spectra of ApoAI-M/ApoAI-M and ApoAI-M/ApoAI-M+DMPC solutions were recorded on a Jasco FP-550 spectroflourometer at 25° C.

Circular dichroism (CD) spectra of ApoAI-M/ApoAI-M and Apo AI-M/ApoAI-M+DMPC solutions were recorded with a Jasco J500A spectropolarimeter at 25° C. Mean residue ellipticity values [THEYA] were expressed in degrees×cm$^2$×dmol$^{-1}$ and were calculated by the equation:

$$[THEYA] = \frac{[THEYA] \times 106}{10 \times l \times c}$$

where [THEYA] is the observed ellipticity in degrees, 106 the mean residue molecular weight of the protein, I the path length in cm, and c the protein concentration in g/ml. The percent alpha-helix was calculated using the equation:

$$\% \text{ alpha-helix} = \frac{[THEYA]_{208 \text{ nm}} - 4{,}000}{33{,}000 - 4{,}000}$$

(Greenfield N, Fasman G D. Computed circular dichroism spectra for the evaluation of protein conformation. Biochemistry 1969; 8:4108–4116)

Electrophoresis

Analytical isoelectric focussing and SDS-PAGE were carried out as previously described (Franceschini G, Sirtori M, Gianfranceschi G, Sirtori C R. Relation between the HDL apoproteins and AI isoproteins in subjects with the AI-M abnormality. Metabolism 1981; 30:502–509).

Isoelectric focusing was performed in 10% acrylamide gels, containing 6 M urea and 4% ampholines (pH 4–6). After overnight focusing, gels were fixed and stained with Coomassie Brilliant Blue R-250 in acetic acid/isopropylic alcohol. The isoelectric point (pI) of any unknown protein bands was calculated by plotting the pI of known proteins (standards from Bio-Rad and apo-HDL) against the respective migration distance.

For SDS-PAGE, 14% acrylamide gels containing 0.1% SDS were used. Gels were treated as described and the molecular weight of unknown proteins calculated from the plot of the logMW of protein standards (KABI-Pharmacia) vs migration distance.

High Performance Size Exclusion Chromatography

Analytical HPSEC separations were carried out using a Jasco liquid chromatograph equipped with a 10 μm TSK-G3000 SW column (7.5×300 mm). The HPSEC column was equilibrated and eluted with 0.1 M phosphate buffer, 0.1 M NaCl, pH 7.2, containing 8 M urea. Proteins were eluted at a flow rate of 0.5 ml/min, and readings made at 220 nm. The peak areas were integrated using a HP-3390 integrator.

Example 6

Manufacture of rHDL Particles Containing ApoAI, ApoAI-M or ApoAI-M/ApoAI-M

Reconstituted high density lipoproteins particles (rHDL) were manufactured using the teqnique presented by Nichols A V et al Biochim. Biophys Acta 750: 353–364(1983) and Matz C E et al J. Biol. Chem. 257:4535–4541 (1982).

Recombinant ApoAI-M dimer (From Example 4) and normal ApoAI, purified from human plasma, were dissolved in 10 mM Tris-HCl, 0.15M NaCl, 0.01% EDTA, 0.006%

NaN$_3$, pH 8.0 (buffer A), containing 4M Gdn-HCl at a concentration of 6 mg/ml. For comparison, the disulfide bond in some of the ApoAI-M/ApoAI-M was reduced by the addition of 20 mM DTT to buffer A+Gdn-HCl. The proteins were dialyzed extensively against buffer A, and diluted to 5.2 mg/ml with the same buffer.

Phospholipids, either egg phosphatidylcholine (EPC) or palmitoyloleylphosphatidylcholine (POPC), were dissolved in CHCl$_3$, dried under N$_2$ and kept under vacuum overnight. Sodium cholate was added at a cholate/PC ratio of 0.55 (w/w); the mixture was vigorously stirred for 3 min at room temperature, and incubated at 40 for 2 h. The protein was then added at a PC/protein weight ratio of 2.17 (POPC) or 2.47 (EPC), and the mixture stirred for 3 min at room temperature and incubated at 4° C. overnight. After dialysis against buffer A for 5 days, the mixture was centrifuged at 11,000 rpm for 5 min in a Beckman Microfuge and the supernatant collected.

The rHDL were separated by nondenaturing polyacrylamine gradient gel electrophoresis (GGE), and particle size determined as previously described by Nichols A V et al in Meth. Enzymol. 128:417–431 (1986).

All tested apolipoproteins almost completely associated with lipids after the described procedure, as demonstrated by the very minor peak of lipid-free apolipoprotein on GGE gels. The recovery of the protein in rHDL varied between 68% to 100% in 10 different preparations.

GGE profiles of reconstituted HDL particles are shown in FIG. 13. HDL reconsituted with ApoAI and EPC gave a major peak on GGE, with a diameter of 9.6 nm; minor components, both of larger and smaller size, were also detectable. The rHDL containing EPC and the ApoAI-M/ApoAI-M consisted of two major (diameter: 8.6 and 12.9 nm) and two minor (diameter 7.9 and 10.8 nm) components (FIG. 13); the same size of particles were obtained when Apo AI-M/ApoAI-M was reconstituted with POPC.

All three apolipoproteins were almost completely incorporated into stable lipid-protein complexes with different rHDL particle sizes, distribution and composition. In particular, rHDL made with recombinant ApoAI-M/ApoAI-M consist of two major components, the larger one being unique among the family of ApoAI-containing rHDL.

BIOLOGICAL EVALUATION of ApoAI-M/ApoAI-M

Example 7

Kinetic Behaviour of ApoAI-M Dimer Versus ApoAI-Monomer in Normal Recipients

Dimers display prolonged persistance in the circulation which has been shown in human kinetic studies below.

The healthy volunteers received i.v. $^{125}$I-labelled ApoAI-M or ApoAI-M/ApoAI-M. As shown in Table 3, the plasma $\beta t_{1/2}$ (h), calculated according to two different models, as well as the fractional catabolic rate (FCR). These both confirm a markedly reduced catabolism of the dimer, vs the monomer.

The very slow catabolism of the ApoAI-M/ApoAI-M indicates that these molecules may impair lipoprotein conversion and possibly act as an effective precursor for ApoAI-M. In this way by the injection of ApoAI-M/ApoAI-M, it can be predicted that the dimer may remain in plasma for a prolonged period of time, thus directly interacting with lipoprotein metabolism and the fibrinolytic system.

TABLE 3

Kinetic behavior of Apa Al-M/Apo Al-M versus Apo Al-Monomer in normal recipients (n = 2)

| | | Apo Al-M | Apo Al-M/Apo Al-M |
|---|---|---|---|
| Monoexponential Mode | $\beta t_{1/2}$ (h) | 16.07 | 52.04 |
| | MRT (h) | 23.19 | 75.09 |
| Biexponential Mode | $\beta t_{1/2}$ (h) | 22.61 | 70.29 |
| | MRT (h) | 28.97 | 89.16 |
| | FCR (h) | 2.3% per hour | 1.1% per hour |

Effect of ApoAI-M/ApoAI-M on the Fibrinolytic System

Introduction

The fibrinolytic system is the major defence against fibrin deposition on vessel walls and as such plays an important role among mechanisms which prevent thrombosis.

The enzyme responsible for the lysis of fibrin is plasmin. Plasmin is formed from the inactive precursor plasminogen by the action of specific activators (tissue plasminogen activator, t-PA and urokinase, uPA). Both the activation process and the action of plasmin are regulated by specific inhibitors—plasminogen activator inhibitor 1 (PAI) and alpha 2-antiplasmin, respectively. Scheme of the fibrinolytic system is presented below.

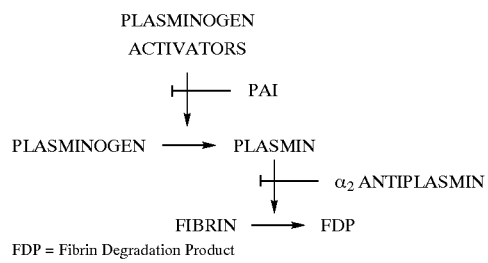

The aim of thepresent investigation in examples 7–9 was to find out how the ApoAI-M dimer affects the human fibrinolytic system. Both autoactivation of plasminogen and its activation with uPA and t-PA were studied in the presence and absence of ApoAI-M/ApoAI-M. Human ApoAI isolated from plasma was used as control (Sigma product nr A 9284)

The activation of the fibrinolytic system was measured with the aid of chromogenic substrates. These substrates contain a chromophore group of paranitroaniline, which can be cleaved from the substrate molecule by the action of plasmin. The free p-NA has an intensive yellow colour, which can easily be followed at 405 nm wavelength. The amount of p-NA released is directly proportional to the amount of generated enzymatic activity.

All measurements were obtained using THERMOmax microplate reader controlled by SOFTmax™ program version 2.01 from Molecular Devices, Menlo Park, Calif., USA.

Batches used in these studies were produced recombinantly according to Example 4. Purification included ion exchange, hydrophobe interaction and gel filtration chromatographies followed by ultrafiltration and freeze-drying—all conventional biochemical methods. All batches investigated contained >90% of dimer form, as indicated by reversed phase HPLC. The concentration was determinated using Kabi Pharmacia apolipoprotein AI RIA 100 assay.

Three preparations, A, B and C were investigated.

Example 8

Auotactivation of Plasminogen in the Presence of ApoAI-M/ApoAI-M and ApoAI

Glu-Plasminogen (94 μg/mL final concentration) was incubated for three hours at. 37° C. in 0.1 mol/L Tris buffer pH 7.6. Plasmin generation was followed with the S-2251 chromogenic substrate (H-D-Val-L-Leu-L-Lys-pNA), obtained from Chromogenix AB, Möndal, Sweden. It was used at 0.6 mmol/L final concentration. Plasminogens applied in these assays were obtained from Chromogenix AB or from IMCO Inc., Stockholm, Sweden.

Batches of ApoAI-M/ApoAI-M (final concentration 3.9–75 μg/mL) were tested in this assay and amount of plasmin generated in their presence compared with the amount of plasmin generated in the presence of ApoAI (125 μg/mL final concentration) and with the amount of plasmin generated in the absence of any additions (control) (Table 4).

It was surprising found that ApoAI-M/ApoAI-M can enhance plasminogen activation in the absence of any plasminogen activators. Plasma-derived ApoAI did not in any way affect the plasminogen molecule.

TABLE 4

Spontaneous generation of plasmin activity in plasminogen. Effect of ApoAI-M/ApoAI-M and ApoAI. Plasmin activity expressed as OD at 405 nm.

| Sample | Apo final conc., μg/mL | OD 405 nm |
| --- | --- | --- |
| Control | 0 | 0.052 |
| +ApoAI | 125 | 0.049 |
| +ApoAI-M/ApoAI-M | | |
| A | 75 | 0.288 |
| B | 31.3 | 0.325 |
| B | 15.6 | 0.153 |
| B | 7.8 | 0.104 |
| B | 3.9 | 0.067 |

The observed activity can be ascribed to ApoAI-M/ApoAI-M. However, on the basis of these data, it can not be excluded that ApoAI-M/ApoAI-M were contaminated by some proteolytic enzyme(s), which could activate plasminogen. Experiments were performed in order to exclude this possibility.

All ApoAI-M/ApoAI-M preparations used in fibrinolytic assays were tested with chromogenic substrates S-2251 (H-D-Val-L-Leu-L-Lys-pNA), sensitive to plasmin-like activity and S-2288 (H-D-lle-Pro-Arg-pNA), sensitive to Arg-specific proteases. Substrates were obtained from Chromogenix AB. The final concentration of ApoAI-M/ApoAI-M in the assays was identical to the one used in the fibrinolytic assays and thus could vary between different batches.

Assay: 25 μL ApoAI-M/ApoAI-M final concentration 60–70 μg/mL

150 μL 0.1 mol/L Tris buffer pH 7.8

50 μL S-2251 0.6 mmol/L or S-2288 1.0 mmol/L

Sample containing only buffer and substrate was used as control for unspecific substrate hydrolysis. All samples were assayed in duplicates.

Microtiter plate was incubated at 37° C. and absorbance was read at hourly intervals.

TABLE 5

Amidolytic activity of two batches of ApoAI-M/ApoAI-M (A and B) after 4 hours incubation at 37° C. (OD at 405 nm).

| | | ApoAI-M/ApoAI-M | Substrat |
| --- | --- | --- | --- |
| S-2251 | A | 0.023 | 0.022 |
| | B | 0.022 | |
| S-2288 | A | 0.037 | 0.034 |
| | B | 0.037 | |

In another series of experiments ApoAI-M/ApoAI-M was treated with an irreversible inhibitor of serine proteases—diisopropyl fluorophosphate, DFP (Sigma product nr D 0789). Final concentration of ApoAI-M/ApoAI-M in 0.2 mol/L KHCO3 pH 7.6 buffer was approximately 75 μg/mL. DFP, 123 mmol/L final concentration, was added to this solution. After 4 hours, the incubation sample was dialysed overnight against two changes of carbonate buffer.

Activity determination, using the same conditions as described earlier, was performed on DFP-treated ApoAI-M/ApoAI-M and on untreated ApoAI-M/ApoAI-M. After a three hour incubation with plasminogen and S-2251, OD at 405 nm was 0.209 for samples containing DFP-treated ApoAI-M/ApoAI-M, 0.234 for samples containing untreated ApoAI-M/ApoAI-M and 0.030 for samples with plasminogen only.

Thus it can be concluded, that the observed plasminogen activating effect is directly connected with the presence of ApoAI-M/ApoAI-M and not due to any potential proteolytic contaminants.

Example 9

Effect of ApoAI-M/ApoAI-M on Activation of Plasminogen With Plasminogen Activators t-PA and uPA Urokinase (uPA) and tissue plasminogen activator (t-PA) both convert plasminogen to plasmin by proteolytic cleavage of a single peptide bond Arg 560-Val 561 in the plasminogen molecule.

Whereas two chain urokinase can activate plasminogen directly, t-PA requires the presence of fibrin for its optimal activation of plasminogen. The presence of catalytic amounts of fibrin, which together with t-PA and plasminogen forms a ternary complex, will increase the enzymatic efficiency of t-PA approximately 600 fold.

The activation of plasminogen with t-PA was studied using commercially available kit Spectrolyse® (fibrin) t-PA/PAI from Biopool AB, Umeå, Sweden.

In this assay plasminogen is incubated with t-PA in the presence of chromogenic substrate D-But-CHT-Lys-pNA and desAA fibrinogen (fibrin monomer); which acts as an activation stimulator. Generated plasmin cleaves substrate, releasing free pNA.

ApoAI-M/ApoAI-M was added to this system and compared with ApoAI preparation from Sigma. The effect of both apolipoproteins was tested in the system both in the presence and absence of fibrin.

Example of the assay system:

25 μL Spectrolyse buffer

25 μL Apo preparation or buffer

20 μL t-PA (=1.7 IU/mL final concentration)

150 μL Spectrolyse PAR reagent (=mixture of plasminogen and substrate)

10 μL Desa fib (=fibrin monomer) or 10 μL buffer

Samples were incubated on microtiterplate at 37° C. for three hours.

TABLE 6

Effect of ApoAl-M/ApoAl-M and ApoAl on plasminogen activation by t-PA in the presence and absence of fibrin. Results are expressed as OD, after 3 hours incubation at 37° C. at 405 nm.

| Sample | Apo final conc., μg/mL | OD 405 nm + fibrin | OD 405 nm − fibrin |
|---|---|---|---|
| t-PA control | 0 | 0.656 | 0.048 |
| +ApoAl | 54 | 1.050 | 0.066 |
| +ApoAl-M/ApoAl-M | | | |
| A | 65 | 1.665 | 0.446 |
| B | 54 | 2.366 | 0.225 |

A significant stimulation of plasminogen activation was observed with ApoAI-M/ApoAI-M, both in the presence and in the absence of fibrin. ApoAI stimulated activation to a lesser degree in the presence of fibrin. In the absence of fibrin the stimulation of ApoAI-M/ApoAI-M was very pronounced compared to the very small stimulation by ApoAI.

ApoAI-M/ApoAI-M had also a significant potentiating effect when plasminogen was activated with uPA. Urokinase used in these assays was a high molecular weight preparation obtained from Calbiochem.

Urokinase (2.5 IU/mL final concentration) was mixed with plasminogen (94 μg/mL final concentration) and chromogenic substrate S-2251 (0.6 mmol/L final concentration). To this sample ApoAI-M/ApoAI-M was added at 75 or 62 μg/mL final concentration. Reaction was performed in 0.1 mol/L Tris buffer, pH 7.6.

Similarly to t-PA, a potent stimulation of plasmin generation by urokinase was observed, when ApoAI-M/ApoAI-M was added to the assay (Table 7).

TABLE 7

Effect of ApoAl-M/ApoAl-M on plasminogen activation by uPA. Results are expressed as OD after 4 hours incubation at 37° C. at 405 nm.

| Sample | ApoAl-M/ApoAl-M Final conc., μg/mL | OD 405 nm |
|---|---|---|
| UPA control | 0 | 0.325 |
| +ApoAl-M/ApoAl-M | | |
| A | 75 | 1.263 |
| B | 62 | 1.868 |

This potentiating effect on fibrinolysis also persisted when ApoAI-M/ApoAI-M was prepared in pharmaceutical composition together with a carrier. As a potential carrier liposomes consisting of phosphatidylcholine, PC, (12 mg/mL) were employed. Concentration of ApoAI-M/ApoAI-M (batch C) in liposomes was 3.6 mg/mL.

Activation of plasminogen (94 μg/mL final conc.) with uPA (2.5 IU/mL final conc.) was tested in the presence of ApoAI-M/ApoAI-M filled liposomes and compared with activation performed in the presence of proteinfree liposomes. Samples were incubated for four hours at 37° C. with S-2251 and plasmin generation followed continuously.

TABLE 8

Activation of plasminogen by UPA. Effect of ApoAl-M/ApoAl-M, batch C. in liposomes. Results are expressed as OD at 405 nm.

| Sample | OD 405 nm |
|---|---|
| uPA + Plasminogen | 0.221 |
| +protein free liposomes, 250 μg/mL PC | 0.499 |
| +ApoAl-M/ApoAl-M 75 μg/mL in liposomes, 250 μg/mL PC | 1.084 |

The presence of liposomes alone stimulated plasminogen activation approximately twofold. Addition of ApoAI-M/ApoAI-M to liposomes increased this effect fivefold—in comparison with sample containing only urokinase activator.

Example 10

Effect of ApoAI-M/ApoAI-M on Conversion of Single Chain Urokinase to Two Chain Urokinase Single chain urokinase (scuPA) is a precursor of two chain urokinase (uPA). In contrast to uPA scuPA has only very low amidolytic activity towards small synthetic substrates. The amidolytic activity is at most 0.4% of the activity of uPA. However, scuPA, in spite of being a proenzyme, has the capacity of activating plasminogen to plasmin. In the mixtures of plasminogen and scuPA a sequence of three reactions has been proposed to be involved in activation of plasminogen to plasmin:

1) scuPA+plasminogen→scuPA+plasmin 2) plasmin+scuPA→plasmin+uPA 3) uPA+plasminogen→uPA+plasmin We studied the sequence of reactions leading to the conversion of scuPA to uPA in the presence of plasminogen. Urokinase activity was detected with the help of urokinase specific chromogenic substrate S-2444 (pyro-Glu-Gly-Arg-pNA, Chromogenix AB).

Batches of ApoAI-M/ApoAI-M and ApoAI were added to the system and amount of generated uPA activity compared with the activity obtained in the samples without apolipoprotein addition. The single chain urokinase used in these assays was a recombinant product obtained from Grunenthal GmbH, Aachen, Germany (lot nr 0088808).

25 μL Apo or buffer

75 μL 0.05 mol/L Tris pH 7.6, containing 0.1 mol/l NaCl and 0.02% Tween 80

25 μL scuPA, 454 pmol/L final concentration

50 μL S-2444, 1 mmol/L final concentration

25 μL plasminogen, 52.1 nmol/L final concentration

Samples were incubated at 37° C. for 90 minutes. The increase in optical density, measuring quantity of generated uPA, was recorded continuously during the last 30 minutes of incubation.

TABLE 9

Effect of ApoAl-M/ApoAl-M on conversion of scuPA to uPA
Results are expressed as mOD/min at 405 nm.

| Sample | Apo final conc., µg/mL | mOD/min |
|---|---|---|
| scuPA | 0 | 0.073 |
| +plasminogen | 0 | 13.2 |
| +ApoAl | 62 | 11.8 |
| +ApoAl-M/ApoAl-M | | |
| B | 62 | 20.0 |
| A | 75 | 24.0 |

Conversion of scuPA to uPA in the presence of plasminogen was stimulated by the ApoAI-M/ApoAI-M, whereas ApoAI isolated from plasma had no significant effect in this system.

The observed effects of ApoAI-M/ApoAI-M on the fibrinolytic assays used in these studies were enhanced compared to the effects seen with ApoAI isolated from plasma. ApoAI-M/ApoAI-M has a potent capacity to stimulate the fibrinolytic activity which is superior to ApoAI. It is likely that this enhanced effect of ApoAI-M/ApoAI-M over ApoAI will also be found in vivo.

What is claimed is:

1. A composition comprising isolated Apolipoprotein-AI-Milano dimer, wherein the dimer comprises two monomers and is purified to at least 90% homogeneity.

2. The composition of claim 1, wherein the dimer is purified to at least 98% homogeneity.

3. The composition of claim 1, wherein the dimer has been isolated from human plasma.

4. The composition of claim 1, wherein the dimer has been recombinantly produced.

5. A pharmacological composition comprising the composition of claim 1 with a pharmaceutically acceptable carrier.

6. A pharmacological composition comprising the composition of claim 1 together with stabilizing lipid compound, optionally with lipid lowering agent, and optionally with a carrier.

7. A pharmacological composition comprising the composition of claim 1 together with a phospholipid, optionally with lipid lowering agent, and optionally with a carrier.

8. A method for the treatment of atherosclerosis or cardiovascular diseases comprising administering the composition of claim 1 in a pharmaceutically acceptable carrier to a patient in need thereof.

9. The method of claim 8 wherein the composition acts as a prodrug for the monomer.

10. The method of claim 8 wherein the cardiovascular diseases are major cardiocirculatory ailments selected from the group consisting of myocardial infarction, unstable angina, acute peripheral vascular occlusions, and restenosis after coronary angioplasty.

11. The method of claim 8 wherein the treatment is a treatment of chronic arterial conditions.

12. The method of claim 8 wherein the treatment is the prevention and treatment of thrombosis.

13. The method of claim 12 for the stimulation of fibrinolysis.

14. A method for the treatment of atherosclerosis or cardiovascular diseases comprising administering isolated Apolipoprotein AI Milano dimer comprising two monomers and purified to at least 90% homogeneity wherein the pharmaceutical composition further comprises a lipid lowering agent.

15. A method for the treatment of atherosclerosis and cardiovascular diseases, comprising administering isolated Apolipoprotein AI Milano dimer comprising two monomers and purified to at least 90% homogeneity, in a therapeutically active amount optionally with added carrier, stabilizing lipid compound and/or lipid lowering agent in a therapeutically active amount.

16. A process for preparing isolated Apolipoprotein AI Milano dimer comprising two monomers and purified to at least 90% homogeneity, comprising:

producing Apolipoprotein-AI-Milano by recombinant technology as an intracellular fusion protein in *E. coli* cleaving the fusion protein, converting any recombinant monomer to the dimer, and purifying the dimer into a substantially pure form.

17. The process of claim 16 comprising cleaving the fusion protein with formic acid.

18. A process for preparing isolated Apolipoprotein AI Milano dimer comprising two monomers and purified to at least 90% homogeneity, comprising: collecting the plasma from Apolipoprotein AI Milano carriers, isolating the HDL apolipoproteins from the plasma, purifying the ApoAIM monomer, converting the ApoAIM monomers into dimers, and purifying the dimer into a substantially pure form.

* * * * *